US005770703A

United States Patent [19]

Alizon et al.

[11] Patent Number: 5,770,703

[45] Date of Patent: Jun. 23, 1998

[54] NUCLEIC ACIDS ENCODING PEPTIDES OF THE ENVELOPE REGION OF HIV-2 AND PEPTIDES, POLYPEPTIDES, AND METHODS FOR PRODUCING THE PEPTIDES AND POLYPEPTIDES OF THE HIV-2 ENVELOPE GENE

[75] Inventors: Marc Alizon, Paris; Luc Montagnier, Le Plessis Robinson; Denise Geutard, Paris, all of France; Francois Clavel, Rockville, Md.; Pierre Sonigo; Mireille Guyader, both of Paris, France

[73] Assignee: Institut Pasteur, Paris, France

[21] Appl. No.: 468,774

[22] Filed: Jun. 6, 1995

Related U.S. Application Data

[60] Continuation of Ser. No. 214,221, Mar. 17, 1994, which is a division of Ser. No. 810,908, Dec. 20, 1991, which is a division of Ser. No. 752,368, Sep. 3, 1991, abandoned, which is a division of Ser. No. 13,477, Feb. 11, 1987, Pat. No. 5,079,342, which is a continuation-in-part of Ser. No. 3,764, Jan. 16, 1987, Pat. No. 5,051,496, which is a continuation-in-part of Ser. No. 933,184, Nov. 21, 1986, abandoned, which is a continuation-in-part of Ser. No. 916,080, Oct. 6, 1986, abandoned, which is a continuation-in-part of Ser. No. 835,228, Mar. 3, 1986, Pat. No. 4,839,288.

[30] Foreign Application Priority Data

| | | | |
|---|---|---|---|
| Jan. 22, 1986 | [FR] | France | 86 00911 |
| Feb. 6, 1986 | [FR] | France | 86 01635 |
| Feb. 13, 1986 | [FR] | France | 86 01985 |
| Mar. 18, 1986 | [FR] | France | 86 03881 |
| Mar. 24, 1986 | [FR] | France | 86 04215 |

[51] Int. Cl.$^6$ .......... C07K 14/155; A61K 39/21; C12Q 1/70; C07H 21/04

[52] U.S. Cl. .......... 530/395; 424/188.1; 435/5; 435/69.1; 435/71.1; 435/252.3; 536/23.72

[58] Field of Search .......... 536/23.72; 435/172.3, 435/69.1, 71.2; 530/324, 325, 326, 395; 424/188.1

[56] References Cited

U.S. PATENT DOCUMENTS

| | | | |
|---|---|---|---|
| 4,629,783 | 12/1986 | Cosand | 530/324 |
| 4,839,288 | 6/1989 | Montagnier et al. | 435/235 |
| 5,079,342 | 1/1992 | Alizon et al. | 530/324 |

FOREIGN PATENT DOCUMENTS

| | | |
|---|---|---|
| 0 316 695 B1 | 3/1993 | European Pat. Off. . |
| WO 85/04897 | 11/1985 | WIPO . |

OTHER PUBLICATIONS

Clavel et al., "Isolation of a New Human Retrovirus from West African Patients with AIDS," *Science,* 233, pp. 343–346 (1986).

Allan et al., "Major Glycoprotein Antigens That Induce Antibodies in AIDS Patients Are Encoded by HTLV–III," *Science,* 228, pp. 1091–1094 (1985).

Chang et al., "Detection of Antibodies to Human T–Cell Lymphotropic Virus–III (HTLV–III) with an Immunoassay Employing a Recombinant *Escherichia coli*–Derived Viral Antigenic Peptide," *Bio/Technology,* 3, pp. 905–909 (1985).

Kanki et al., "Isolation of T–lymphotropic Retrovirus Related to HTLV–III/LAV from Wild–Caught African Green Monkeys," *Science,* 230, pp. 951–954 (1985).

Kanki et al., "Serologic Identification and Characterization of a Macaque T–lymphotropic Retrovirus Closely Related to HTLV–III," *Science,* 228, pp. 1199–1201 (1985).

Clavel et al., "LAV Type II: A Second Retrovirus Associated With AIDS In West Africa," *C.R. Acad. Sc. Paris,* Serie III, 302, pp. 485–488 (1986).

Klatzmann et al., "T–lymphocyte T4 Molecule Behaves As The Receptor For Human Retrovirus LAV," *Nature,* 312, pp. 767–768 (1984).

Daniel et al., "Isolation of T–Cell Tropic HTLV–III–like Retrovirus from Macaques," *Science,* 228, pp. 1201–1204 (1985).

Barin et al., "Serological Evidence For Virus Related To Simian T–lymphotropic Retrovirus III in Residents of West Africa," *The Lancet,* pp. 1387–1389 (Dec. 21/28, 1985).

Sandstrom et al., "Antiviral Therapy In AIDS Clinical Pharmacological Properties and Therapeutic Experience to Date," *Drugs,* 34, pp. 372–390 (1987).

Mitsuya et al., "Protection of T Cells Against Infectivity and Cytopathic Effect of HTLV–III In Vitro," Retroviruses in Human Lymphoma/Leukemia, M. Miwa et al., eds., pp. 277–288 (Japan Science Press, Tokyo, 1985).

Gallo et al., "HIV/HTLV gene nomenclature". Nature 333:564 (1988).

Laurence, J., "Summary of HIV–1 and HIV–2 nomenclature", AIDS Res. Hum. Retro. 4:vii–viii (1988).

(a) Clavel et al., "Isolation of a new human retrovirus from West African patients with AIDS", Science 233:343–347 (1986).

(b) Clavel et al., "Molecular cloning and polymorphism of the human immunodeficiency virus type 2", Nature 324:691–695 (1986).

*Primary Examiner*—Robert D. Budens
*Assistant Examiner*—Jeffrey S. Parkin
*Attorney, Agent, or Firm*—Finnegan, Henderson, Farabow, Garrett & Dunner, L.L.P.

[57] ABSTRACT

The inventors disclose nucleic acids of HIV-2 encoding the entire envelope glycoprotein and peptide regions thereof. Also described are purified and cloned nucleic acids having the entire HIV-2 genome. The nucleic acids can be used to produce polypeptides corresponding to the HIV-2 envelope gene or peptides from specific regions of the HIV-2 envelope gene. Uses in hybridization assays are also disclosed.

6 Claims, 11 Drawing Sheets

ENVELOPE SEQUENCE

ThrTrpTyrSerLysAspValValCysGluThrAsnAsnSerThr
ACATGGTACTCAAAAGATGTGGTTTGTGAGACAAATAATAGCACA

AsnGlnThrGlnCysTyrMetAsnHisCysAsnThrSerValIle
AATCAGACCCAGTGTTACATGAACCATTGCAACACATCAGTCATC
600

ThrGluSerCysAspLysHisTyrTrpAspAlaIleArgPheArg
ACAGAATCATGTGACAAGCACTATTGGGATGCTATAAGGTTTAGA

TyrCysAlaProProGlyTyrAlaLeuLeuArgCysAsnAspThr
TACTGTGCACCACCGGGTTATGCCCTATTAAGATGTAATGATACC
700

AsnTyrSerGlyPheAlaProAsnCysSerLysValValAlaSer
AATTATTCAGGCTTTGCACCCAACTGTTCTAAAGTAGTAGCTTCT

ThrCysThrArgMetMetGluThrGlnThrSerThrTrpPheGly
ACATGCACCAGGATGATGGAAACGCAAACTTCCACATGGTTTGGC
800

PheAsnGlyThrArgAlaGluAsnArgThrTyrIleTyrTrpHis
TTTAATGGCACTAGAGCAGAGAATAGAACATATATCTATTGGCAT

GlyArgAspAsnArgThrIleIleSerLeuAsnLysTyrTyrAsn
GGCAGAGATAATAGAACTATCATCAGCTTAAACAAATATTATAAT
900

LeuSerLeuHisCysLysArgProGlyAsnLysThrValLysGln
CTCAGTTTGCATTGTAAGAGGCCAGGGAATAAGACAGTGAAACAA

IleMetLeuMetSerGlyHisValPheHisSerHisTyrGlnPro
ATAATGCTTATGTCAGGACATGTGTTTCACTCCCACTACCAGCCG

*FIG. 6B-1*

```
IleAsnLysArgProArgGlnAlaTrpCysTrpPheLysGlyLys
ATCAATAAAAGACCCAGACAAGCATGGTGCTGGTTCAAAGGCAAA
          1000

TrpLysAspAlaMetGlnGluValLysThrLeuAlaLysHisPro
TGGAAAGACGCCATGCAGGAGGTGAAGACCCTTGCAAAACATCCC

ArgTyrArgGlyThrAsnAspThrArgAsnIleSerPheAlaAla
AGGTATAGAGGAACCAATGACACAAGGAATATTAGCTTTGCAGCG
                          1100

ProGlyLysGlySerAspProGluValAlaTyrMetTrpThrAsn
CCAGGAAAAGGCTCAGACCCAGAAGTAGCATACATGTGGACTAAC

CysArgGlyGluPheLeuTyrCysAsnMetThrTrpPheLeuAsn
TGCAGAGGAGAGTTTCTCTACTGCAACATGACTTGGTTCCTCAAT
                                    1200

TrpIleGluAsnLysThrHisArgAsnTyrAlaProCysHisIle
TGGATAGAGAATAAGACACACCGCAATTATGCACCGTGCCATATA

LysGlnIleIleAsnThrTrpHisLysValGlyArgAsnValTyr
AAGCAAATAATTAACACATGGCATAAGGTAGGGAGAAATGTATAT
                                              1300

LeuProProArgGluGlyGluLeuSerCysAsnSerThrValThr
TTGCCTCCCAGGGAAGGGGAGCTGTCCTGCAACTCAACAGTAACC

SerIleIleAlaAsnIleAspTrpGlnAsnAsnAsnGlnThrAsn
AGCATAATTGCTAACATTGACTGGCAAAACAATAATCAGACAAAC

IleThrPheSerAlaGluValAlaGluLeuTyrArgLeuGluLeu
ATTACCTTTAGTGCAGAGGTGGCAGAACTATACAGATTGGAGTTG
 1400
```

FIG. 6B-2

ENVELOPESEQUENCE

```
GlyAspTyrLysLeuValGluIleThrProIleGlyPheAlaPro
GCAGATTATAAATTGGTAGAAATAACACCAATTGGCTTCGCACCT

ThrLysGluLysArgTyrSerSerAlaHisGlyArgHisThrArg
ACAAAAGAAAAAAGATACTCCTCTGCTCACGGGAGACATACAAGA
            1500

GlyValPheValLeuGlyPheLeuGlyPheLeuAlaThrAlaGly
GGTGTGTTCGTGCTAGGGTTCTTGGGTTTTCTCGCAACAGCAGGT

SerAlaMetGlyAlaArgAlaSerLeuThrValSerAlaGlnSer
TCTGCAATGGGCGCTCGAGCGTCCCTGACCGTGTCGGCTCAGTCC
                        1600

ArgThrLeuLeuAlaGlyIleValGlnGlnGlnGlnGlnLeuLeu
CGGACTTTACTGGCCGGGATAGTGCAGCAACAGCAACAGCTGTTG

AspValValLysArgGlnGlnGluLeuLeuArgLeuThrValTrp
GACGTGGTCAAGAGACAACAAGAACTGTTGCGACTGACCGTCTGG
                                    1700

GlyThrLysAsnLeuGlnAlaArgValThrAlaIleGluLysTyr
GGAACGAAAAACCTCCAGGCAAGAGTCACTGCTATAGAGAAGTAC

LeuGlnAspGlnAlaArgLeuAsnSerTrpGlyCysAlaPheArg
CTACAGGACCAGGCGCGGCTAAATTCATGGGGATGTGCGTTTAGA
                                            1800

GlnValCysHisThrThrValProTrpValAsnAspSerLeuAla
CAAGTCTGCCACACTACTGTACCATGGGTTAATGATTCCTTAGCA

ProAspTrpAspAsnMetThrTrpGlnGluTrpGluLysGlnVal
CCTGACTGGGACAATATGACGTGGCAGGAATGGGAAAAACAAGTC
```

*FIG. 6C-1*

```
ArgTyrLeuGluAlaAsnIleSerLysSerLeuGluGlnAlaGln
CGCTACCTGGAGGCAAATATCAGTAAAAGTTTAGAACAGGCACAA
      1900

IleGlnGlnGluLysAsnMetTyrGluLeuGlnLysLeuAsnSer
ATTCAGCAAGAGAAAAATATGTATGAACTACAAAAATTAAATAGC

TrpAspIlePheGlyAsnTrpPheAspLeuThrSerTrpValLys
TGGGATATTTTTGGCAATTGGTTTGACTTAACCTCCTGGGTCAAG
                  2000

TyrIleGlnTyrGlyValLeuIleIleValAlaValIleAlaLeu
TATATTCAATATGGAGTGCTTATAATAGTAGCAGTAATAGCTTTA

ArgIleValIleTyrValValGlnMetLeuSerArgLeuArgLys
AGAATAGTGATATATGTAGTACAAATGTTAAGTAGGCTTAGAAAG
                       2100

GlyTyrArgProValPheSerSerProProGlyTyrIleGln***
GGCTATAGGCCTGTTTTCTCTTCCCCCCCCGGTTATATCCAATAG

IleHisIleHisLysAspArgGlyGlnProAlaAsnGluGluThr
ATCCATATCCACAAGGACCGGGGACAGCCAGCCAACGAAGAAACA
                               2200

GluGluAspGlyGlySerAsnGlyGlyAspArgTyrTrpProTrp
GAAGAAGACGGTGGAAGCAACGGTGGAGACAGATACTGGCCCTGG

ProIleAlaTyrIleHisPheLeuIleArgGlnLeuIleArgLeu
GCGATAGCATATATACATTTCCTGATCCGCCAGCTGATTCGCCTC

LeuThrArgLeuTyrSerIleCysArgAspLeuLeuSerArgSer
TTGACCAGACTATACAGCATCTGCAGGGACTTACTATCCAGGAGC
    2300
```

FIG. 6C-2

ENV1(1732-1809)

```
                         ArgValThrAlaIleGluLysTyr
                         AGAGTCACTGCTATAGAGAAGTAC

LeuGlnAspGlnAlaArgLeuAsnSerTrpGlyCysAlaPheArg
CTACAGGACCAGGCGCGGCTAAATTCATGGGGATGTGCGTTTAGA
                                          1000
GlnValCys
CAAGTCTGC
```

ENV2(1912-1983)

```
                         SerLysSerLeuGluGlnAlaGln
                         AGTAAAAGTTTAGAACAGGCACAA

IleGlnGlnGluLysAsnMetTyrGluLeuGlnLysLeuAsaSer
ATTCAGCAAGAGAAAAATATGTATGAACTACAAAAATTAAATAGC
 1940
Trp
TGG
```

ENV3(1482-1530)

```
ProThrLysGluLysArgTyrSerSerAlaHisGlyArgHisThrArg
CCTACAAAAGAAAAAAGATACTCCTCTGCTCACGGGAGACATACAAGA
               1500
```

ENV4(55-129)

```
        CysThrGlnTyrValThrValPheTyrGlyValPro
        TGCACCCAATATGTAACTGTTTTCTATGGCGTACCC

ThrTrpLysAsnAlaThrIleProLeuPheCysAlaThr
ACGTGGAAAAATGCAACCATTCCCCTGTTTTGTGCAACC
       100
```

FIG. 7A-1

ENV5(175-231)

```
                                                  AspAsp
                                                  GATGAT

TyrGlnGluIleThrLeuAsnValThrGluAlaPheAspAlaTrp
TATCAGGAAATAACTTTGAATGTAACAGAGGCTTTTGATGCATGG
                         200
AsnAsn
AATAAT
```

ENV6(274-330)

```
      GluThrSerIleLysProGysValLysLeuThrProLeuCys
      GAGACATCAATAAAACCATGTGTGAAACTAACACCTTTATGT
                               300
ValAlaMetLysCys
GTAGCAATGAAATGC
```

ENV7(607-660)

```
                  AsnHisCysAsnThrSerValIle
                  AACCATTGCAACACATCAGTCATC
                  610
ThrGluSerCysAspLysHisTyrTrpAsp
ACAGAATCATGTGACAAGCACTATTGGGAT
```

FIG. 7A-2

NUCLEIC ACIDS ENCODING PEPTIDES OF THE ENVELOPE REGION OF HIV-2 AND PEPTIDES, POLYPEPTIDES, AND METHODS FOR PRODUCING THE PEPTIDES AND POLYPEPTIDES OF THE HIV-2 ENVELOPE GENE

This is a continuation of application Ser. No. 08/214,221, filed Mar. 17, 1994, which is a divisional of application Ser. No. 07/810,908, filed Dec. 20, 1991, which is a divisional of application Ser. No. 07/752,368, filed Sep. 3, 1991, now abandoned, which is a divisional of application Ser. No. 07/013,477, filed Feb. 11, 1987, (now U.S. Pat. No. 5,079, 342), which is a CIP of application Ser. No. 07/003,764, filed Jan. 16, 1987, (now U.S. Pat. No. 5,051,496), which is a CIP of application Ser. No. 06/933,184, filed Nov. 21, 1986, now abandoned, which is a CIP of application Ser. No. 06/916, 080, filed Oct. 6, 1986, now abandoned, which is a CIP of application Ser. No. 06/835,228, filed Mar. 3, 1986, now U.S. Pat. No. 4,839,288).

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core portion of their infecting virus, it is important to include antigens to both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolate, subsequently referred to as LAV-II MIR, was deposited at the Collection Nationale des Cultures de Micro-Organismes (CNCM) at the Institut Pasteur in Paris, France on Dec. 19, 1985 under Accession No. I-502 and has also been deposited at the British ECA CC under No. 87.001.001 on Jan. 9, 1987. A second LAV-II isolate was deposited at CNCM on Feb. 21, 1986 under Accession No. I-532 and has also been deposited at the British ECA CC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. I-643). Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to: (1) Southern blot procedures to identify viral DNA which may or may not be digested with restriction enzymes; (2) Northern blot techniques to identify viral RNA extracted from cells; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes of nuclei of the cells by ultracentrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

To further achieve the objects of the invention, a vaccinating agent is provided which comprises at least one peptide selected from the polypeptide expression products of the viral DNA in admixture with suitable carriers, adjuvents stabilizers.

It is understood that both the foregoing general description and the following detailed description are exemplary and explanatory only and are not restrictive of the invention as claimed. The accompanying drawings, which are incorporated in and constitute a part of the specification, illustrate one embodiment of the invention and, together with the description, serve to explain the principles of the invention.

BRIEF DESCRIPTION OF THE DRAWINGS

FIG. 1A depicts the genetic organization of HIV-1, position of the HIV-1 HindIII fragment used as a probe to screen the cDNA library, and restriction map of the HIV-2 cDNA clone, E2. FIG. 1B depicts the nucleotide sequence of the 3' end of HIV-2. The corresponding region of the HIV-1 LTR was aligned using the Wilbur and Lipman algorithm (window: 10; K-tuple; 7; gap penalty: 3) as described by Wilbur and Lipman in Proc. Natl. Acad. Sci. USA 80: 726–730 (1983), specifically incorporated herein by reference. The U3-R junction in HIV-1 is indicated and the poly A addition signal and potential TATA promoter regions are boxed. In FIG. 1B, the symbols B, H, Ps and Pv refer to the restriction sites BamHI, HindIII, PstI and PvuII, respectively.

FIG. 2A and 2B specifically depict a Southern blot of DNA extracted from CEM cells infected with the following isolates: HIV-$2_{ROD}$ (a,c), HIV-$2_{DUL}$ (b,d), and HIV-$1_{BRU}$ (e,f). DNA in lanes a,b,f was Pst I digested; in c,d,e DNA was undigested. FIG. 2C and 2D specifically depict dot blot hybridization of pelleted virions from CEM cells infected by the HIV-$1_{BRU}$(1), Simian Immunodeficiency Virus (SIV) isolate Mm 142-83 (3), HIV-$2_{DUL}$ (4), HIV-$2_{ROD}$ (5), and HIV-$1_{ELI}$ (6). Dot 2 is a pellet from an equivalent volume of supernatant from uninfected CEM. Thus, FIG. 2A and 2C depicts hybridization with the HIV-2 cDNA (E2) and FIG. 2B and 2D depicts hybridization to an HIV-1 probe consisting of a 9Kb SacI insert from HIV-1 BRU(clone lambda J 19).

FIG. 3A specifically depicts the organization of three recombinant phage lambda clones, ROD 4, ROD 27, and ROD 35. In FIG. 3A, the open boxes represent viral sequences, the LTR are filled, and the dotted boxes represent cellular flanking sequences (not mapped). Only some characteristic restriction enzyme sites are indicated. λROD 27 and λROD 35 are derived from integrated proviruses while λROD 4 is derived from a circular viral DNA. The portion of the lambda clones that hybridzes to the cDNA E2 is indicated below the maps. A restriction map of the λROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 3B specifically depicts dots 1–11 which correspond to the single-stranded DNA form of M13 subclones from the HIV-$1_{BRU}$ cloned genome (λJ19). Their size and position on the HIV-1 genome, determined by sequencing is shown below the figure. DOT 12 is a control containing lambda phage DNA. The dot-blot was hybridized in low stringency conditions as described in Example 1 with the complete lambda λROD 4 clone as a probe, and successively washed in 2×SSC, 0.1% SDS at 25° C. (Tm −42° C.), 1×SSC, 0.1% SDS at 60° C. (Tm −20° C.), and 0.1×SSC, 0.1% SDS at 60° C. (Tm −3° C.) and exposed overnight. A duplicate dot blot was hybridized and washed in stringent conditions (as described in Example 2) with the labelled lambda J19 clone carrying the complete HIV-$1_{BRU}$ genome. HIV-1 and HIV-2 probes were labelled the same specific activity ($10^8$ cpm/g.).

FIG. 4A specifically depicts DNA (20 ug. per lane) from CEM cells infected by the isolate HIV-$2_{DUL}$ (panel 1) or peripheral blood lymphocytes (PBL) infected by the isolates HIV-$2_{GOM}$ (panel 2) and HIV-$2_{MIR}$ (panel 3) digested with: EcoRI (a), PstI (b), and HindIII (c). Much less viral DNA was obtained with HIV-2 isolates propagated on PBL. Hybridization and washing were in stringent conditions, as described in Example 2, with $10^6$ cpm/ml. of each of the E2 insert (cDNA) and the 5 kb. HindIII fragment of λROD 4, labelled to $10^9$ cpm/ug.

FIG. 4B specifically depicts DNA from HUT 78 (a human T lymphoid cell line) cells infected with STLV3 MAC isolate Mm 142-83. The same amounts of DNA and enzymes were used as indicated in panel A. Hybridization was performed with the same probe as in A, but in non-stringent conditions. As described in Example 1 washing was for one hour in 2×SSC, 0.1% SDS at 40° C. (panel 1) and after exposure, the same filter was re-washed in 0.1× SSC, 0.1% SDS at 60° C. (panel 2). The autoradiographs were obtained after overnight exposition with intensifying screens.

FIG. 6 depicts the combined nucleotide sequence and corresponding amino acid sequence of the envelope protein.

FIG. 7 depicts the combined nucleotide sequence and corresponding amino acid sequences for each of env1, env2, env3, env4, env5, env6, env7, env8, env9, env10, env11, and gag1.

DETAILED DESCRIPTION OF THE PREFERRED EMBODIMENTS

Reference will now be made in detail to the presently preferred embodiments of the invention, which, together with the following examples, serve to explain the principles of the invention.

Figure 1A:
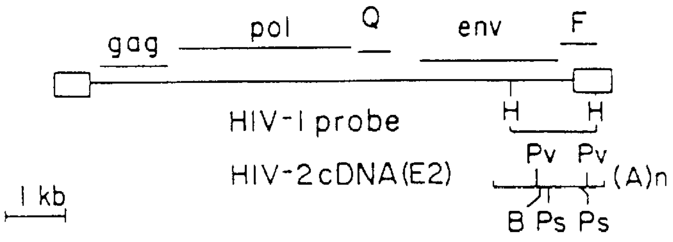
FIGS. 1A and 1B generally depict the nucleotide sequence of a cloned complementary DNA (cDNA) to the genomic RNA of HIV-2.
Figure 1B:

The genetic structure of the HIV-2 virus has been analyzed by molecular cloning according to the method set forth herein and in the Examples. A restriction map of the genome of this virus is included in FIG. 4. In addition, the partial sequence of a cDNA complementary to the genomic RNA of the virus has been determined. This cDNA sequence information is included in FIG. 1.

Also contained herein is data describing the molecular cloning of the complete 9.5 kb genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the gag and pol genes were conducted. These hybridizations yielded only extremely weak signals even in conditions of very low stringency of hybrization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al. in Cancer 18: 522–529 (1965), specifically incorporated herein by reference. The CEM cells used were infected with the isolate ROD and were continuously producing high amounts of HIV-2.

After second-strand synthesis, the cDNAs were inserted into the M 13 tg 130 bacteriophage vector. A collection of $10^4$ M13 recombinant phages was obtained and screened in situ with an HIV-1 probe spanning 1.5 kb. of the 3' end of the $LAV_{BRU}$ isolate (depicted in FIG. 1A). Some 50 positive plaques were detected, purified, and characterized by end sequencing and cross-hybridizing the inserts. This procedure is described in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in Cell 40: 9–17 (1985), specifically incorporated herein by reference. The portion of the HIV-2 LTR that was sequenced was related only distantly to the homologous domain in HIV-1 as demonstrated in FIG. 1B. Indeed, only about 50% of the nucleotides could be aligned and about a hundred insertions/deletions need to be introduced. In comparison, the homology of the corresponding domains in HIV-1 isolates from USA and Africa is greater than 95% and no insertions or deletions are seen.

Figures 2A, 2B, 2C, 2D:
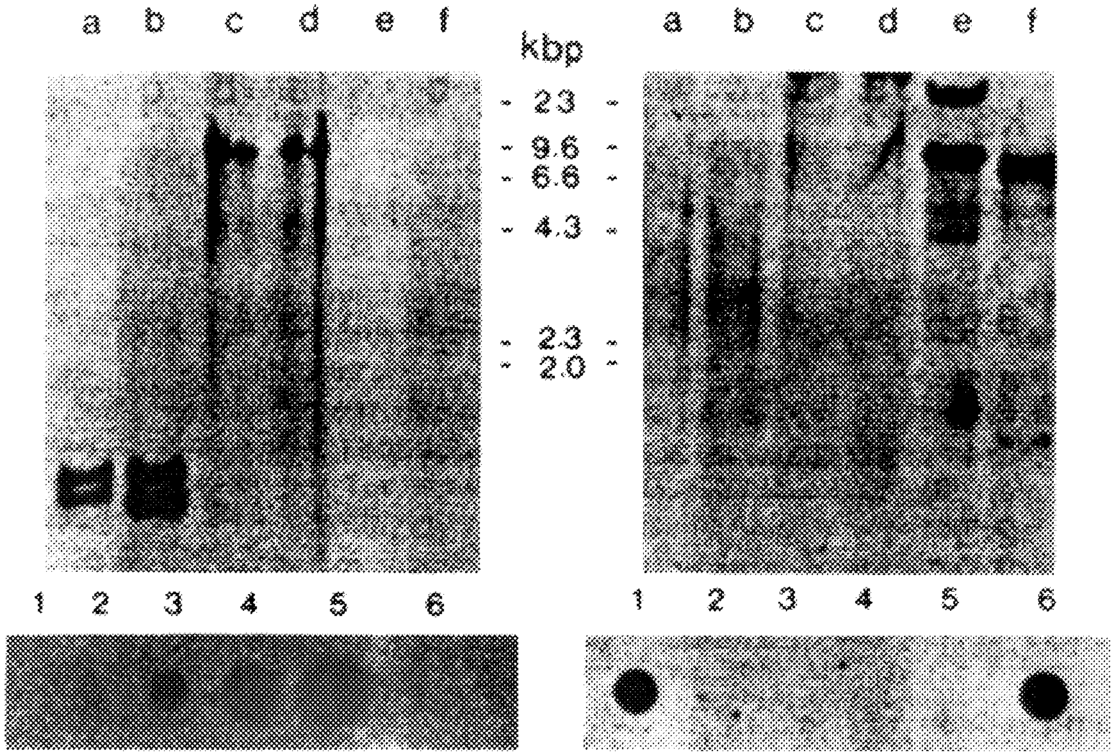
FIGS. 2A–2D generally depict the HIV-2 specificity of the E2 clone.

The largest insert of this group of M13 clones was a 2 kb. clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIG. 2, C and D. Secondly, positive signals were detected in Southern blots of DNA from cells infected with the ROD isolate as well as other isolates of HIV-2 as shown in FIG. 2, A and FIG. 4, A. No signal was detected with DNA from uninfected cells or HIV-1 infected cells, confirming the exogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization to HIV-1 infected cells only as depicted in FIG. 2, B.

To isolate the remainder of the genome of HIV-2, a genomic library in lambda phage L47.1 was constructed. Lambda phage L47.1 has been described by W. A. M. Loenen et al. in Gene 10: 249–259 (1980), specifically incorporated herein by reference. The genomic library was constructed with a partial Sau3AI restriction digest of the DNA from the CEM cell line infected with $HIV\text{-}2_{ROD}$.

About $2\times10^6$ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figure 3A:
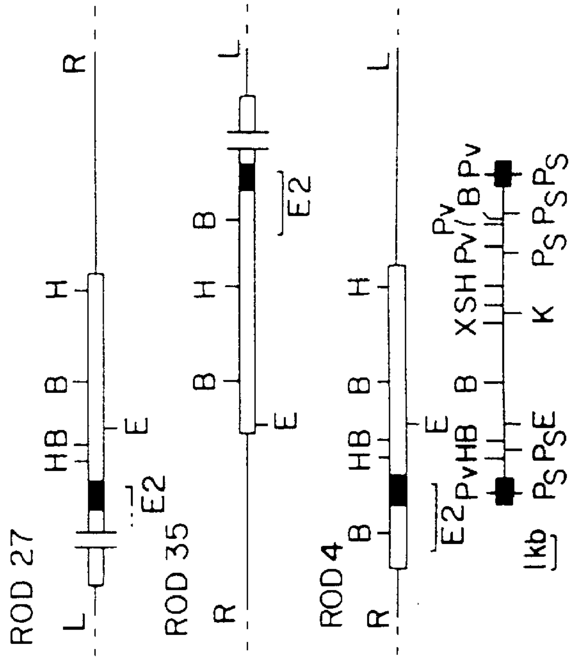
FIGS. 3A and 3B generally depict a restriction map of the HIV-2 ROD genome and its homology to HIV-1.
Figure 3B:
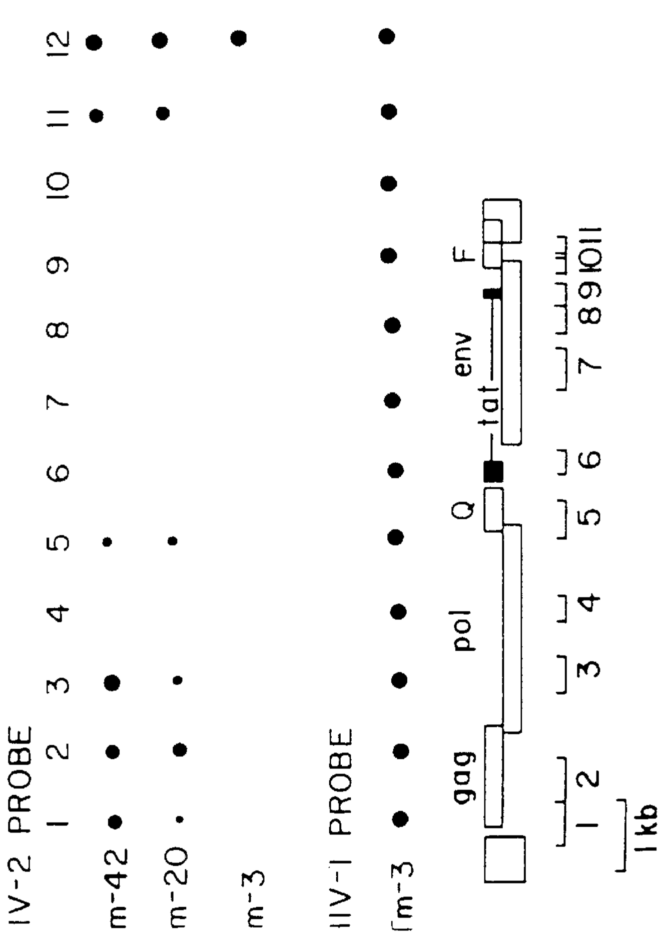

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3, A.

Fragments of the lambda clones were subcloned into a plasmid vector p UC 18.

Plasmid pROD 27-5' is derived from λROD 27 and contains the 5' 2Kb of the HIV-2 genome and cellular flanking sequences (5' LTR and 5' viral coding sequences to the EcoRI site).

Plasmid p ROD 4-8 is derived from λROD 4 and contains the about 5 kb HindIII fragment that is the central part of the HIV-2 genome.

Plasmid pROD 27-5' and p ROD 4.8 inserts overlap.

Plasmid pROD 4.7 contains a HindIII 1.8 Kb fragment from λROD 4. This fragment is located 3' to the fragment subcloned into pROD 4.8 and contains about 0.8 Kb of viral coding sequences and the part of the lambda phage (λL47.1) left arm located between the BamHl and HindIII cloning sites.

Plasmid pROD 35 contains all the HIV-2coding sequences 3' to the EcoRI site, the 3' LTR and about 4 Kb of cellular flanking sequences.

Figure 5:
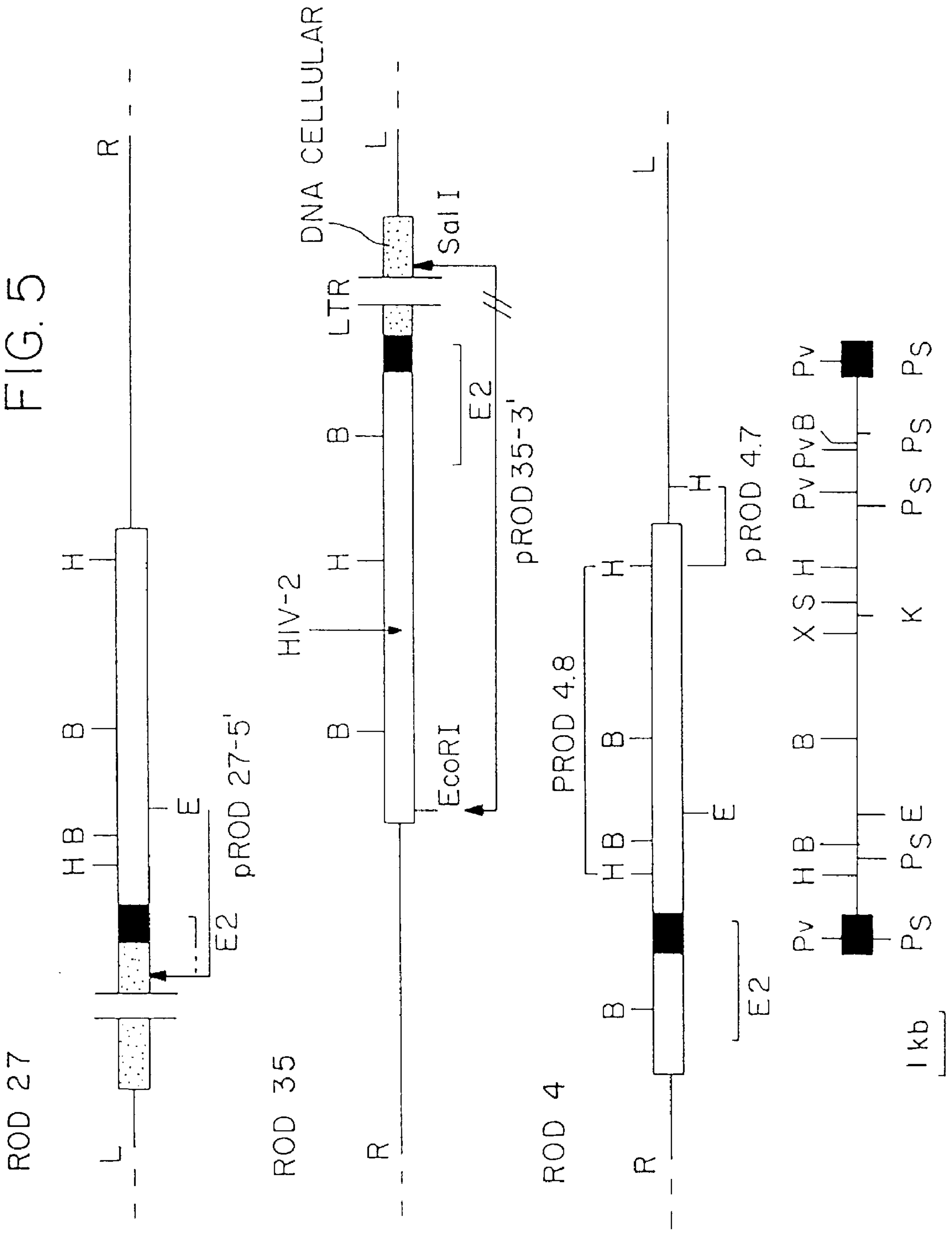
FIG. 5 depicts the position of derived plasmids from λROD 27, λROD 35 and λROD 4.

Plasmid pROD 27-5' and pROD 35 in *E. coli* strain HB 101 are deposited respectively under No. 1-626 and 1- 633 at the CNCM, and have also been deposited at the NCIB (British Collection). These plasmids are depicted in FIG. 5. Plasmids pROD 4-7 and pROD 4-8 in *E. coli* strain TG1 1are deposited respectively under No. 1-627 and 1-628 at the CNCM.

To reconstitute the complete HIV-2 ROD genome, pROD 35 is linearized with EcoRi and the EcoRI insert of pROD 27-5' is ligated in the correct orientation into this site.

The relationship of HIV-2 to other human and simian retroviruses was surmised from hybridization experiments. The relative homology of the different regions of the HIV-1 and 2 genomes was determined by hybridization of fragments of the cloned HIV-1 genome with the labelled λROD 4 expected to contain the complete HIV-2 genome (FIG. 3, B). Even in very low stringency conditions (Tm −42° C.), the hybridization of HIV-1 and 2 was restricted to a fraction of their genomes, principally the gag gene (dots 1 and 2), the reverse transcriptase domain in pol (dot 3), the end of pol and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of the pol thus seemed very divergent. These data, along with the LTR sequence obtained (FIG. 1, B), indicated that HIV-2 is not an envelope variant of HIV-1, as are African isolates from Zaire described by Alizon et al., *Cell* 40:63–74 (1986).

It was observed that HIV-2 is related more closely to the Simian Immunodeficiency Virus (SIV) than it is to HIV-1. This correlation has been described by F. Clavel et al. in C. R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotropic Virus Type 3, STLV-3) is a retrovirus first isolated from captive macaques with an AIDS-like disease in the USA. This simian virus has been described by M. D. Daniel et al. in Science 228: 1201–1204 (1985), specifically incorporated herein by reference.

All the SIV proteins, including the envelope, are immune precipitated by sera from HIV-2 infected patients, whereas the serological cross-reactivity of HIV-1 to 2 is restricted to the core proteins. However SIV and HIV-2 can be distinguished by slight differences in the apparent molecular weight of their proteins.

In terms of nucleotide sequence, it also appears that HIV-2 is closely related to SIV. The genomic RNA of SIV can be detected in stringent conditions as shown in FIG. 2, C by HIV-2 probes corresponding to the LTR and 3' end of the genome (E2) or to the gag or pol genes. Under the same conditions, HIV-1 derived probes do not detect the SIV genome as shown in FIG. 2, D.

In Southern blots of DNA from SIV-infected cells, a restriction pattern clearly different from HIV-$2_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

Figure 4A:
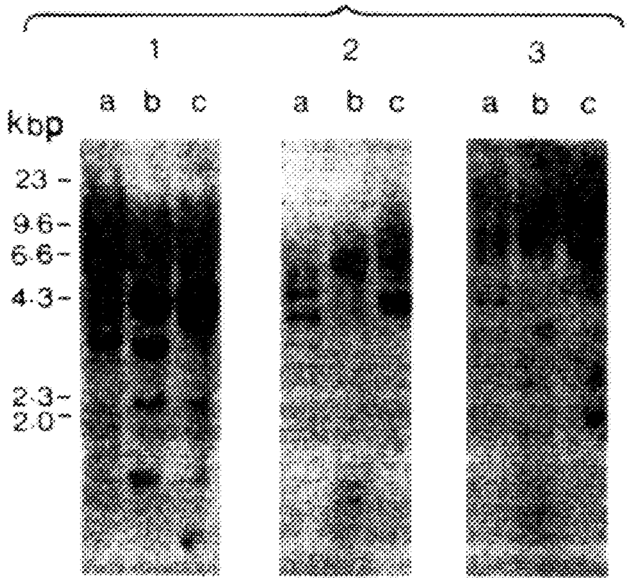
FIGS. 4A and 4B generally depict the restriction map polymorphism in different HIV-2 isolates and shows comparison of HIV-2 and SIV.
Figure 4B:
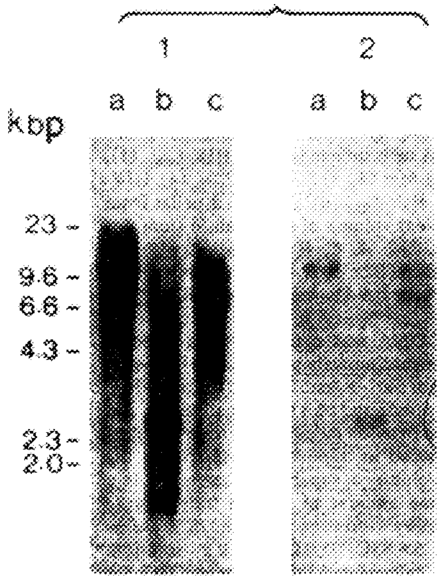

From an initial survey of the restriction maps for certain of the HIV-2 isolates obtained according to the methods described herein, it is already apparent that HIV-2, like HIV-1, undergoes restriction site polymorphism. FIG. 4 A depicts examples of such differences for three isolates, all different one from another and from the cloned HIV-$2_{ROD}$. It is very likely that these differences at the nucleotide level are accompanied by variations in the amino-acid sequence of the viral proteins, as evidenced in the case of HIV-1 and described by M. Alizon et al. in Cell 46: 63–74 (1986), specifically incorporated herein by reference. It is also to be expected that the various isolates of HIV-2 will exhibit amino acid heterogeneities. See, for example, Clavel et al., *Nature* 324 (18):691–695 (1986), specifically incorporated herein by reference.

Further, the chacterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could be used to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of ROD 4 and the E2 cDNA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides or fragments thereof may be created. The monoclonal antibodies may be used in immunodiagnostic tests in an analogous manner as the polypeptides described above.

The polypeptides of the present invention may also be used as immunogenic reagents to induce protection against infection by HIV-2 viruses. In this embodiment, the polypeptides produced by recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

Example 1

Cloning of a cDNA Complementary to Genomic RNA from HIV-2 Virions

HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in Nature, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Gubler and Hoffman in Gene, 25: 263–269 (1983), specifically incorporated herein by reference, using a commercial cDNA synthesis kit obtained from Amersham. After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the *E. coli* TG1 strain. Recombinant plaques ($10^4$) were screened in situ on replica filters with the 1.5 kb. HindIII fragment from clone J19, corresponding to the 3' part of the genome of the $LAV_{BRU}$ isolate of HIV-1, $^{32}P$ labelled to a specific activity of $10^9$ cpm ug. The filters were prehybridized in 5×SSC, 5×Denhardt solution, 25% formamide, and denatured salmon sperm DNA (100 ug/ml.) at 37° C. for 4 hours and hybridized for 16 hours in the same buffer (Tm −42° C.) plus $4\times10^7$ cpm of the labelled probe ($10^6$ cpm/ml. of hybridization buffer). The washing was done in 5×SSC, 0.1% SDS at 25° C. for 2 hours. 20×SSC is 3M NaCl, 0.3M Na citrate. Positive plaques were purified and single-stranded M13 DNA prepared and end-sequenced according to the method described in Proc. Nat'l. Acad. Sci. USA, 74: 5463–5467 (1977) of Sanger et al.

Example 2

Hybridization of DNA from HIV-1 and HIV-2 Infected Cells and RNA from HIV-1 and 2 and SIV Virons With a Probe Derived From an HIV-2 Cloned cDNA DNA was extracted from infected CEM cells continuously producing HIV-1 or 2. The DNA digested with 20 ug of PstI digested with or undigested, was electrophoresed on a 0.8% agarose gel, and Southern-transferred to nylon membrane. Virion dot-blots were prepared in duplicate, as described by F. Clavel et al. in Science 233: 343–346 (1986), specifically incorporated herein by reference, by pelleting volumes of supernatant corresponding to the same amount of reverse transcriptase activity. Prehybridizaton was done in 50% formamide, 5×SSC, 5×Denhardt solution, and 100 mg./ml. denatured salmon sperm DNA for 4 hours at 420 C. Hybridization was performed in the same buffer plus 11% Dextran sulphate, and $10^6$ cpm/ml. of the labelled E2 insert (specific activity $10^9$ cpm/ug.) for 16 hours at 42° C. Washing was in 0.1×SSC, 0.1% SDS for 2×30 mn. After exposition for 16 hours with intensifying screens, the Southern blot was dehybridized in 0.4N NaOH, neutralized, and rehybridized in the same conditions to the HIV-1 probe labelled to $10^9$ cpm/ug.

Example 3

Cloning in Lambda Phage of the Complete Provirus DNA of HIV-2

DNA from the HIV-$2_{ROD}$ infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques ($2\times10^6$) obtained after in vitro packaging and plating on *E. coli* LA 101 strain were screened in situ with the insert from the E2 cDNA clone. Approximately 10 positive clones were plaque purified and propagated on *E. coli* C600 recBC. The ROD 4, 27, and 35 clones were amplified and their DNA characterized by restriction mapping and Southern blotting with the HIV-2 cDNA clone under stringent conditions, and gag-pol probes from HIV-1 used under non stringent conditions.

Example 4

Complete Genomic Sequence of the ROD HIV-2 Isolate

Experimental analysis of the HIV-2 ROD isolate yielded the following sequence which represents the complete genome of this HIV-2 isolate. Genes and major expression products identified within the following sequence are indicated by nucleotides numbered below:

1) GAG gene (546–2111) expresses a protein product having a molecular weight of around 55 Kd and is cleaved into the following proteins:
   a) p 16 (546–950)
   b) p 26 (951–1640)
   c) p 12 (1701–2111)
2) polymerase (1829–4936)
3) Q protein (4869–5513)
4) R protein (5682–5996)
5) X protein (5344–5679)
6) Y protein (5682–5996)
7) Env protein (6147–8720)
8) F protein (8557–9324)
9) TAT gene (5845–6140 and 8307–8400) is expressed by two exons separated by introns.
10) ART protein (6071–6140) and 8307–8536) is similarly the expression product of two exons.
11) LTR:R (1–173 and 9498–9671)
12) U5 (174–299)
13) U3 (8942–9497)

It will be known to one of skill in the art that the absolute numbering which has been adopted is not essential. For example, the nucleotide within the LTR which is designated as "1" is a somewhat arbitrary choice. What is important is the sequence information provided.

```
GGTCGCTCTGCGGAGAGGCTGGCAGATTGAGCCCTGGGAGGTTCTCTCCAGCACTAGCAG
         •         •         •         •         •         •
GTAGAGCCTGGGTGTTCCCTGCTAGACTCTCACCAGCACTTGGCCGGTGCTGGGCAGACG
         •         •         •        100        •         •
GCCCCACGCTTGCTTGCTTAAAAACCTCTTAATAAAGCTGCCAGTTAGAAGCAAGTTAAG
         •         •         •         •         •         •
TGTGTGCTCCCATCTCTCCTAGTCGCCGCCTGGTCATTCGGTGTTCACCTGAGTAACAAG
         •        200        •         •         •         •
ACCCTGGTCTGTTAGGACCCTTCTTGCTTTGGGAAACCGAGGCAGGAAAATCCCTAGCAG
         •         •         •         •         •        300
GTTGGCGCCTGAACAGGGACTTGAAGAAGACTGAGAAGTCTTGGAACACGGCTGAGTGAA
         •         •         •         •         •         •
GGCAGTAAGGGCGGCAGGAACAAACCACGACGGAGTGCTCCTAGAAAGGCGCGGGCCGAG
         •         •         •        400        •         •
```

-continued

```
GTACCAAAGGCAGCGTGTGGAGCGGGAGGAGAAGAGGCCTCCGGGTGAAGGTAAGTACCT

ACACCAAAAACTGTAGCCGAAAGGGCTTGCTATCCTACCTTTAGACAGGTAGAAGATTGT
          500
    Met Gly Ala Arg Asn Ser Val Leu Arg Gly Lys Lys Ala Asp Glu Leu Glu Arg Ile
GGGAGATGGGCGCGAGAAACTCCGTCTTGAGAGGGAAAAAAGCAGATGAATTAGAAAGAA
                                                          600
 Arg Leu Arg Pro Gly Gly Lys Lys Lys Tyr Arg Leu Lys His Ile Val Trp Ala Ala Asn
TCAGGTTACGGCCCGGCGGAAAGAAAAAGTACAGGCTAAAACATATTGTGTGGGCAGCGA

 Lys Leu Asp Arg Phe Gly Leu Ala Glu Ser Leu Leu Glu Ser Lys Glu Gly Cys Gln Lys
ATAAATTGGACAGATTCGGATTAGCAGAGAGCCTGTTGGAGTCAAAAGAGGGTTGTCAAA
                                    700
 Ile Leu Thr Val Leu Asp Pro Met Val Pro Thr Gly Ser Glu Asn Leu Lys Ser Leu Phe
AAATTCTTACAGTTTTAGATCCAATGGTACCGACAGGTTCAGAAAATTTAAAAAGTCTTT

 Asn Thr Val Cys Val Ile Trp Cys Ile His Ala Glu Glu Lys Val Lys Asp Thr Glu Gly
TTAATACTGTCTGCGTCATTTGGTGCATACACGCAGAAGAGAAAGTGAAAGATACTGAAG
          800
 Ala Lys Gln Ile Val Arg Arg His Leu Val Ala Glu Thr Gly Thr Ala Glu Lys Met Pro
GAGCAAAACAAATAGTGCGGAGACATCTAGTGGCAGAAACAGGAACTGCAGAGAAAATGC
                                                          900
 Ser Thr Ser Arg Pro Thr Ala Pro Ser Ser Glu Lys Gly Gly Asn Tyr Pro Val Gln His
CAAGCACAAGTAGACCAACAGCACCATCTAGCGAGAAGGGAGGAAATTACCCAGTGCAAC

 Val Gly Gly Asn Tyr Thr His Ile Pro Leu Ser Pro Arg Thr Leu Asn Ala Trp Val Lys
ATGTAGGCGGCAACTACACCCATATACCGCTGAGTCCCCGAACCCTAAATGCCTGGGTAA
                                    1000
 Leu Val Glu Glu Lys Lys Phe Gly Ala Glu Val Val Pro Gly Phe Gln Ala Leu Ser Glu
AATTAGTAGAGGAAAAAAAGTTCGGGGCAGAAGTAGTGCCAGGATTTCAGGCACTCTCAG

 Gly Cys Thr Pro Tyr Asp Ile Asn Gln Met Leu Asn Cys Val Gly Asp His Gln Ala Ala
AAGGCTGCACGCCCTATGATATCAACCAAATGCTTAATTGTGTGGGCGACCATCAAGCAG
          1100
 Met Gln Ile Ile Arg Glu Ile Ile Asn Glu Glu Ala Ala Glu Trp Asp Val Gln Lis Pro
CCATGCAGATAATCAGGGAGATTATCAATGAGGAAGCAGCAGAATGGGATGTGCAACATC
                                                          1200
 Ile Pro Gly Pro Leu Pro Ala Gly Gln Leu Arg Glu Pro Arg Gly Ser Asp Ile Ala Gly
CAATACCAGGCCCCTTACCAGCGGGGCAGCTTAGAGAGCCAAGGGGATCTGACATAGCAG

    Thr Thr Ser Thr Val Glu Glu Gln Ile Gln Trp Met Phe Arg Pro Gln Asn Pro Val Pro
    GGACAACAAGCACAGTAGAAGAACAGATCCAGTGGATGTTTAGGCCACAAAATCCTGTAC
                                        1300
    Val Gly Asn Ile Tyr Arg Arg Trp Ile Gln Ile Gly Leu Gln Lys Cys Val Arg Met Tyr
    CAGTAGGAAACATCTATAGAAGATGGATCCAGATAGGATTGCAGAAGTGTGTCAGGATGT

    Asn Pro Thr Asn Ile Leu Asp Ile Lys Gln Gly Pro Lys Glu Pro Phe Gln Ser Tyr Val
    ACAACCCGACCAACATCCTAGACATAAAACAGGGACCAAAGGAGCCGTTCCAAAGCTATG
              1400
    Asp Arg Phe Tyr Lys Ser Leu Arg Ala Glu Gln Thr Asp Pro Ala Val Lys Asn Trp Met
    TAGATAGATTCTACAAAAGCTTGAGGGCAGAACAAACAGATCCAGCAGTGAAGAATTGGA
                                                              1500
    Thr Gln Thr Leu Leu Val Gln Asn Ala Asn Pro Asp Cys Lys Leu Val Leu Lys Gly Leu
    TGACCCAAACACTGCTAGTACAAAATGCCAACCCAGACTGTAAATTAGTGCTAAAAGGAC

    Gly Met Asn Pro Thr Leu Glu Glu Met Leu Thr Ala Cys Gln Gly Val Gly Gly Pro Gly
    TAGGGATGAACCCTACCTTAGAAGAGATGCTGACCGCCTGTCAGGGGGTAGGTGGCCCAG
                                        1600
    Gln Lys Ala Arg Leu Met Ala Glu Ala Leu Lys Glu Val Ile Gly Pro Ala Pro Ile Pro
    GCCAGAAAGCTAGATTAATGGCAGAGGCCCTGAAAGAGGTCATAGGACCTGCCCCTATCC

    Phe Ala Ala Ala Gln Gln Arg Lys Ala Phe Lys Cys Trp Asn Cys Gly Lys Glu Gly His
    CATTCGCAGCAGCCCAGCAGAGAAAGGCATTTAAATGCTGGAACTGTGGAAAGGAAGGGC
              1700
    Ser Ala Arg Gln Cys Arg Ala Pro Arg Arg Gln Gly Cys Trp Lys Cys Gly Lys Pro Gly
    ACTCGGCAAGACAATGCCGAGCACCTAGAAGGCAGGGCTGCTGGAAGTGTGGTAAGCCAG
                                                              1800
                                      Thr Gly Arg Phe Phe Arg Thr Gly Pro Leu Gly
    His Ile Met Thr Asn Cys Pro Asp Arg Gln Ala Gly Phe Leu Gly Leu Gly Pro Trp Gly
    GACACATCATGACAAACTGCCCAGATAGACAGGCAGGTTTTTTAGGACTGGGCCCTTGGG

  Lys Glu Ala Pro Gln Leu Pro Arg Gly Pro Ser Ser Ala Gly Ala Asp Thr Asn Ser Thr
    Lys Lys Pro Arg Asn Phe Pro Val Ala Gln Val Pro Gln Gly Leu Thr Pro Thr Ala Pro
    GAAAGAAGCCCCGCAACTTCCCCGTGGCCCAAGTTCCGCAGGGGCTGACACCAACAGCAC
                                        1900
  Pro Ser Gly Ser Ser Ser Gly Ser Thr Gly Glu Ile Tyr Ala Ala Arg Glu Lys Thr Glu
    Pro Val Asp Pro Ala Val Asp Leu Leu Glu Lys Tyr Met Gln Gln Gly Lys Arg Gln Arg
    CCCCAGTGGATCCAGCAGTGGATCTACTGGAGAAATATATGCAGCAAGGGAAAAGACAGA

  Arg Ala Glu Arg Glu Thr Ile Gln Gly Ser Asp Arg Gly Leu Thr Ala Pro Arg Ala Gly
    Glu Gln Arg Glu Arg Pro Tyr Lys Glu Val Thr Glu Asp Leu Leu His Leu Glu Gln Gly
    GAGAGCAGAGAGAGAGACCATACAAGGAAGTGACAGAGGACTTACTGCACCTCGAGCAGG
              2000
```

-continued

```
Gly Asp Thr Ile Gln Gly Ala Thr Asn Arg Gly Leu Ala Ala Pro Gln Phe Ser Leu Trp
 Glu Thr Pro Tyr Arg Glu Pro Pro Thr Glu Asp Leu Leu His Leu Asn Ser Leu Phe Gly
GGGAGACACCATACAGGGAGCCACCAACAGAGGACTTGCTGCACCTCAATTCTCTCTTTG
                                                        2100
Lys Arg Pro Val Val Thr Ala Tyr Ile Glu Gly Gln Pro Val Glu Val Leu Leu Asp Thr
 Lys Asp Gln
GAAAAGACCAGTAGTCACAGCATACATTGAGGGTCAGCCAGTAGAAGTCTTGTTAGACAC

Gly Ala Asp Asp Ser Ile Val Ala Gly Ile Glu Leu Gly Asn Asn Tyr Ser Pro Lys Ile
AGGGGCTGACGACTCAATAGTAGCAGGAATAGAGTTAGGGAACAATTATAGCCCAAAAAT
                                    2200
Val Gly Gly Ile Gly Gly Phe Ile Asn Thr Lys Glu Tyr Lys Asn Val Glu Ile Glu Val
AGTAGGGGGAATAGGGGGATTCATAAATACCAAGGAATATAAAAATGTAGAAATAGAAGT

Leu Asn Lys Lys Val Arg Ala Thr Ile Met Thr Gly Asp Thr Pro Ile Asn Ile Phe Gly
TCTAAATAAAAAGGTACGGGCCACCATAATGACAGGCGACACCCCAATCAACATTTTTGG
                2300
Arg Asn Ile Leu Thr Ala Leu Gly Met Ser Leu Asn Leu Pro Val Ala Lys Val Glu Pro
CAGAAATATTCTGACAGCCTTAGGCATGTCATTAAATCTACCAGTCGCCAAAGTAGAGCC
                                                        2400
Ile Lys Ile Met Leu Lys Pro Gly Lys Asp Gly Pro Lys Leu Arg Gln Trp Pro Leu Thr
AATAAAAATAATGCTAAAGCCAGGGAAAGATGGACCAAAACTGAGACAATGGCCCTTAAC

Lys Glu Lys Ile Glu Ala Leu Lys Glu Ile Cys Glu Lys Met Glu Lys Glu Gly Gln Leu
AAAAGAAAAAATAGAAGCACTAAAAGAAATCTGTGAAAAAATGGAAAAAGAAGGCCAGCT
                                    2500
Glu Glu Ala Pro Pro Thr Asn Pro Tyr Asn Thr Pro Thr Phe Ala Ile Lys Lys Lys Asp
AGAGGAAGCACCTCCAACTAATCCTTATAATACCCCCACATTTGCAATCAAGAAAAAGGA

Lys Asn Lys Trp Arg Met Leu Ile Asp Phe Arg Glu Leu Asn Lys Val Thr Gln Asp Phe
CAAAAACAAATGGAGGATGCTAATAGATTTCAGAGAACTAAACAAGGTAACTCAAGATTT
                2600
Thr Glu Ile Gln Leu Gly Ile Pro His Pro Ala Gly Leu Ala Lys Lys Arg Arg Ile Thr
CACAGAAATTCAGTTAGGAATTCCACACCCAGCAGGGTTGGCCAAGAAGAGAAGAATTAC
                                                        2700
Val Leu Asp Val Gly Asp Ala Tyr Phe Ser Ile Pro Leu His Glu Asp Phe Arg Pro Tyr
TGTACTAGATGTAGGGGATGCTTACTTTTCCATACCACTACATGAGGACTTTAGACCATA

Thr Ala Phe Thr Leu Pro Ser Val Asn Asn Ala Glu Pro Gly Lys Arg Tyr Ile Tyr Lys
TACTGCATTTACTCTACCATCAGTGAACAATGCAGAACCAGGAAAAAGATACATATATAA
                                    2800
Val Leu Pro Gln Gly Trp Lys Gly Ser Pro Ala Ile Phe Gln His Thr Met Arg Gln Val
AGTCTTGCCACAGGGATGGAAGGGATCACCAGCAATTTTTCAACACACAATGAGACAGGT

Leu Glu Pro Phe Arg Lys Ala Asn Lys Asp Val Ile Ile Ile Gln Tyr Met Asp Asp Ile
ATTAGAACCATTCAGAAAAGCAAACAAGGATGTCATTATCATTCAGTACATGGATGATAT
                2900
Leu Ile Ala Ser Asp Arg Thr Asp Leu Glu His Asp Arg Val Val Leu Gln Leu Lys Glu
CTTAATAGCTAGTGACAGGACAGATTTAGAACATGATAGGGTAGTCCTGCAGCTCAAGGA
                                                        3000
Leu Leu Asn Gly Leu Gly Phe Ser Thr Pro Asp Glu Lys Phe Gln Lys Asp Pro Pro Tyr
ACTTCTAAATGGCCTAGGATTTTCTACCCCAGATGAGAAGTTCCAAAAAGACCCTCCATA

His Trp Met Gly Tyr Glu Leu Trp Pro Thr Lys Trp Lys Leu Gln Lys Ile Gln Leu Pro
CCACTGGATGGGCTATGAACTATGGCCAACTAAATGGAAGTTGCAGAAAATACAGTTGCC
                                    3100
Gln Lys Glu Ile Trp Thr Val Asn Asp Ile Gln Lys Leu Val Gly Val Leu Asn Trp Ala
CCAAAAAGAAATATGGACAGTCAATGACATCCAGAAGCTAGTGGGTGTCCTAAATTGGGC

Ala Gln Leu Tyr Pro Gly Ile Lys Thr Lys His Leu Cys Arg Leu Ile Arg Gly Lys Met
AGCACAACTCTACCCAGGGATAAAGACCAAACACTTATGTAGGTTAATCAGAGGAAAAAT
                3200
Thr Leu Thr Glu Glu Val Gln Trp Thr Glu Leu Ala Glu Ala Glu Leu Glu Glu Asn Arg
GACAGTCACAGAAGAAGTACAGTGGACAGAATTACCAGAAGCAGAGCTAGAAGAAAACAG
                                                        3300
Ile Ile Leu Ser Gln Glu Gln Glu Gly His Tyr Tyr Gln Glu Glu Lys Glu Leu Glu Ala
AATTATCCTAAGCCAGGAACAAGAGGGACACTATTACCAAGAAGAAAAAGAGCTAGAAGC

Thr Val Gln Lys Asp Gln Glu Asn Gln Trp Thr Tyr Lys Ile His Gln Glu Glu Lys Ile
AACAGTCCAAAAGGATCAAGAGAATCAGTGGACATATAAAATACACCAGGAAGAAAAAAT
                                    3400
Leu Lys Val Gly Lys Tyr Ala Lys Val Lys Asn Thr His Thr Asn Gly Ile Arg Leu Leu
TCTAAAAGTAGGAAAATATGCAAAGGTGAAAAACACCCATACCAATGGAATCAGATTGTT

Ala Gln Val Val Gln Lys Ile Gly Lys Glu Ala Leu Val Ile Trp Gly Arg Ile Pro Lys
AGCACAGGTAGTTCAGAAAATAGGAAAAGAAGCACTAGTCATTTGGGGACGAATACCAAA
                3500
Phe His Leu Pro Val Glu Arg Glu Ile Trp Glu Gln Trp Trp Asp Asn Tyr Trp Gln Val
ATTTCACCTACCAGTAGAGAGAGAAATCTGGGAGCAGTGGTGGGATAACTACTGGCAAGT
                                                        3600
Thr Trp Ile Pro Asp Trp Asp Phe Val Ser Thr Pro Pro Leu Val Arg Leu Ala Phe Asn
GACATGGATCCCAGACTGGGACTTCGTGTCTACCCCACCACTGGTCAGGTTAGCGTTTAA
```

-continued

```
Leu Val Gly Asp Pro Ile Pro Gly Ala Glu Thr Phe Tyr Thr Asp Gly Ser Cys Asn Arg
CCTGGTAGGGGATCCTATACCAGGTGCAGAGACCTTCTACACAGATGGATCCTGCAATAG
3700
Gln Ser Lys Glu Gly Lys Ala Gly Tyr Val Thr Asp Arg Gly Lys Asp Lys Val Lys Lys
GCAATCAAAAGAAGGAAAAGCAGGATATGTAACAGATAGAGGGAAAGACAAGGTAAAGAA
Leu Glu Gln Thr Thr Asn Gln Gln Ala Glu Leu Glu Ala Phe Ala Met Ala Leu Thr Asp
ACTAGAGCAAACTACCAATCAGCAAGCAGAACTAGAAGCCTTTGCGATGGCACTAACAGA
3800
Ser Gly Pro Lys Val Asn Ile Ile Val Asp Ser Gln Tyr Val Met Gly Ile Ser Ala Ser
CTCGGGTCCAAAAGTTAATATTATAGTAGACTCACAGTATGTAATGGGGATCAGTGCAAG
3900
Gln Pro Thr Glu Ser Glu Ser Lys Ile Val Asn Gln Ile Ile Glu Glu Met Ile Lys Lys
CCAACCAACAGAGTCAGAAAGTAAAATAGTGAACCAGATCATAGAAGAAATGATAAAAAA
Glu Ala Ile Tyr Val Ala Trp Val Pro Ala His Lys Gly Ile Gly Gly Asn Gln Glu Val
GGAAGCAATCTATGTTGCATGGGTCCCAGCCCACAAAGGCATAGGGGGAAACCAGGAAGT
4000
Asp His Leu Val Ser Gln Gly Ile Arg Gln Val Leu Phe Leu Glu Lys Ile Glu Pro Ala
AGATCATTTAGTGAGTCAGGGTATCAGACAAGTGTTGTTCCTGGAAAAAATAGAGCCCGC
Gln Glu Glu His Glu Lys Tyr His Ser Asn Val Lys Glu Leu Ser His Lys Phe Gly Ile
TCAGGAAGAACATGAAAAATATCATAGCAATGTAAAAGAACTGTCTCATAAATTTGGAAT
4100
Pro Asn Leu Val Ala Arg Gln Ile Val Asn Ser Cys Ala Gln Cys Gln Gln Lys Gly Glu
ACCCAATTTAGTGGCAAGGCAAATAGTAAACTCATGTGCCCAATGTCAACAGAAAGGGGA
4200
Ala Ile His Gly Gln Val Asn Ala Glu Leu Gly Thr Trp Gln Met Asp Cys Thr His Leu
AGCTATACATGGGCAAGTAAATGCAGAACTAGGCACTTGGCAAATGGACTGCACACATTT
Glu Gly Lys Ile Ile Ile Val Ala Val His Val Ala Ser Gly Phe Ile Glu Ala Glu Val
AGAAGGAAAGATCATTATAGTAGCAGTACATGTTGCAAGTGGATTTATAGAAGCAGAAGT
4300
Ile Pro Gln Glu Ser Gly Arg Gln Thr Ala Leu Phe Leu Leu Lys Leu Ala Ser Arg Trp
CATCCCACAGGAATCAGGAAGACAAACAGCACTCTTCCTATTGAAACTGGCAAGTAGGTG
Pro Ile Thr His Leu His Thr Asp Asn Gly Ala Asn Phe Thr Ser Gln Glu Val Lys Met
GCCAATAACACACTTGCATACAGATAATGGTGCCAACTTCACTTCACAGGAGGTGAAGAT
4400
Val Ala Trp Trp Ile Gly Ile Glu Gln Ser Phe Gly Val Pro Tyr Asn Pro Gln Ser Gln
GGTAGCATGGTGGATAGGTATAGAACAATCCTTTGGAGTACCTTACAATCCACAGAGCCA
4500
Gly Val Val Glu Ala Met Asn His His Leu Lys Asn Gln Ile Ser Arg Ile Arg Glu Gln
AGGAGTAGTAGAAGCAATGAATCACCATCTAAAAAACCAAATAAGTAGAATCAGAGAACA
Ala Asn Thr Ile Glu Thr Ile Val Leu Met Ala Ile His Cys Met Asn Phe Lys Arg Arg
GGCAAATACAATAGAAACAATAGTACTAATGGCAATTCATTGCATGAATTTTAAAAGAAG
4600
Gly Gly Ile Gly Asp Met Thr Pro Ser Glu Arg Leu Ile Asn Met Ile Thr Thr Glu Gln
GGGGGGAATAGGGGATATGACTCCATCAGAAAGATTAATCAATATGATCACCACAGAACA
Glu Ile Gln Phe Leu Gln Ala Lys Asn Ser Lys Leu Lys Asp Phe Arg Val Tyr Phe Arg
AGAGATACAATTCCTCCAAGCCAAAAATTCAAAATTAAAAGATTTTCGGGTCTATTTCAG
4700
Glu Gly Arg Asp Glu Leu Trp Lys Gly Pro Gly Glu Leu Leu Trp Lys Gly Glu Gly Ala
AGAAGGCAGAGATCAGTTGTGGAAAGGACCTGGGGAACTACTGTGGAAAGGAGAAGGAGC
4800
Val Leu Val Lys Val Gly Thr Asp Ile Lys Ile Ile Pro Arg Arg Lys Ala Lys Ile Ile
AGTCCTAGTCAAGGTAGGAACAGACATAAAAATAATACCAAGAAGGAAAGCCAAGATCAT
Arg Asp Tyr Gly Gly Arg Gln Glu Met Asp Ser Gly Ser His Leu Glu Gly Ala Arg Glu
        Met Glu Glu Asp Lys Arg Trp Ile Val Val Pro Thr Trp Arg Val Pro Gly Arg
CAGAGACTATGGAGGAAGACAAGAGATGGATAGTGGTTCCCACCTGGAGGGTGCCAGGGA
4900
Asp Gly Glu Met Ala
 Met Glu Lys Trp His Ser Leu Val Lys Tyr Leu Lys Tyr Lys Thr Lys Asp Leu Glu Lys
GGATGGAGAAATGGCATAGCCTTGTCAAGTATCTAAAATACAAAACAAAGGATCTAGAAA
 Val Cys Tyr Val Pro His His Lys Val Gly Trp Ala Trp Trp Thr Cys Ser Arg Val Ile
AGGTGTGCTATGTTCCCCACCATAAGGTGGGATGGGCATGGTGGACTTGCAGCAGGGTAA
5000
  Phe Pro Leu Lys Gly Asn Ser His Leu Glu Ile Gln Ala Tyr Trp Asn Leu Thr Pro Glu
  TATTCCCATTAAAAGGAAACAGTCATCTAGAGATACAGGCATATTGGAACTTAACACCAG
5100
  Lys Gly Trp Leu Ser Ser Tyr Ser Val Arg Ile Thr Trp Tyr Thr Glu Lys Phe Trp Thr
  AAAAAGGATGGCTCTCCTCTTATTCAGTAAGAATAACTTGGTACACAGAAAAGTTCTGGA
  Asp Val Thr Pro Asp Cys Ala Asp Val Leu Ile His Ser Thr Tyr Phe Pro Cys Phe Thr
  CAGATGTTACCCCAGACTGTGCAGATGTCCTAATACATAGCACTTATTTCCCTTGCTTTA
5200
  Ala Gly Glu Val Arg Arg Ala Ile Arg Gly Glu Lys Leu Leu Ser Cys Cys Asn Tyr Pro
  CAGCAGGTGAAGTAAGAAGAGCCATCAGAGGGGAAAAGTTATTGTCCTGCTGCAATTATC
```

-continued

Arg Ala His Arg Ala Gln Val Pro Ser Leu Gln Phe Leu Ala Leu Val Val Val Gln Gln
CCCGAGCTCATAGAGCCCAGGTACCGTCACTTCAATTTCTGGCCTTAGTGGTAGTGCAAC
• 5300 • • •

Met Thr Asp Pro Arg Glu Thr Val Pro Pro Gly Asn Ser Gly Glu Glu Thr Ile Gly
Asn Asp Arg Pro Gln Arg Asp Ser Thr Thr Arg Lys Gln Arg Arg Arg Asp Tyr Arg Arg
AAAATGACAGACCCCAGAGAGACAGTACCACCAGGAAACAGCGGCGAAGAGACTATCGGA
• • • • 5400

Glu Ala Phe Ala Trp Leu Asn Arg Thr Val Glu Ala Ile Asn Arg Glu Ala Val Asn His
Gly Leu Arg Leu Ala Lys Gln Asp Ser Arg Ser His Lys Gln Arg Ser Ser Glu Ser Pro
GAGGCCTTCGCCTGGCTAAACAGGACAGTAGAAGCCATAAACAGAGAAGCAGTGAATCAC
• • • • •

Leu Pro Arg Glu Leu Ile Phe Gln Val Trp Gln Arg Ser Trp Arg Tyr Trp His Asp Glu
Thr Pro Arg Thr Tyr Phe Pro Gly Val Ala Glu Val Leu Glu Ile Leu Ala
CTACCCCGAGAACTTATTTTCCAGGTGTGGCAGAGGTCCTGGAGATACTGGCATGATGAA
• • • 5500 • •

Gln Gly Met Ser Glu Ser Tyr Thr Lys Tyr Arg Tyr Leu Cys Ile Ile Gln Lys Ala Val
CAAGGGATGTCAGAAAGTTACACAAAGTATAGATATTTGTGCATAATACAGAAAGCAGTG
• • • • • •

Tyr Met His Val Arg Lys Gly Cys Thr Cys Leu Gly Arg Gly His Gly Pro Gly Gly Trp
TACATGCATGTTAGGAAAGGGTGTACTTGCCTGGGGAGGGGACATGGGCCAGGAGGGTGG
• 5600 • • •

Arg Pro Gly Pro Pro Pro Pro Pro Pro Pro Gly Leu Val
Met Ala Glu Ala Pro Thr Glu
AGACCAGGGCCTCCTCCTCCTCCCCCTCCAGGTCTGGTCTAATGGCTGAAGCACCAACAG
• • • • 5700

Leu Pro Pro Val Asp Gly Thr Pro Leu Arg Glu Pro Gly Asp Glu Trp Ile Ile Glu Ile
AGCTCCCCCCGGTGGATGGGACCCCACTGAGGGAGCCAGGGGATGAGTGGATAATAGAAA
• • • • • •

Leu Arg Glu Ile Lys Glu Glu Ala Leu Lys His Phe Asp Pro Arg Leu Leu Ile Ala Leu
TCTTGAGAGAAATAAAAGAAGAAGCTTTAAAGCATTTTGACCCTCGCTTGCTAATTGCTC
• • • 5800 • •

Met Glu Thr Pro Leu Lys Ala Pro Glu Ser Ser Leu
Gly Lys Tyr Ile Tyr Thr Arg His Gly Asp Thr Leu Glu Gly Ala Arg Glu Leu Ile Lys
TTGGCAAATATATCTATACTAGACATGGAGACACCCTTGAAGGCGCCAGAGAGCTCATTA
• • • • • •

Lys Ser Cys Asn Glu Pro Phe Ser Arg Thr Ser Glu Gln Asp Val Ala Thr Gln Glu Leu
Val Leu Gln Arg Ala Leu Phe Thr His Phe Arg Ala Gly Cys Gly His Ser Arg Ile Gly
AAGTCCTGCAACGAGCCCTTTTCACGCACTTCAGAGCAGGATGTGGCCACTCAAGAATTG
• 5900 • • •

Ala Arg Gln Gly Glu Glu Ile Leu Ser Gln Leu Tyr Arg Pro Leu Glu Thr Cys Asn Asn
Gln Thr Arg Gly Gly Asn Pro Leu Ser Ala Ile Pro Thr Pro Arg Asn Met Gln
GCCAGACAAGGGGAGGAAATCCTCTCTCAGCTATACCGACCCCTAGAAACATGCAATAAC
• • • • 6000

Ser Cys Tyr Cys Lys Arg Cys Cys Tyr His Cys Gln Met Cys Phe Leu Asn Lys Gly Leu
TCATGCTATTGTAAGCCATGCTGCTACCATTGTCAGATGTGTTTTCTAAACAAGGGGCTC
• • • • • •

Gly Ile Cys Tyr Glu Arg Lys Gly Arg Arg Arg Arg Thr Pro Lys Lys Thr Lys Thr His
Met Asn Glu Arg Ala Asp Glu Glu Gly Leu Gln Arg Lys Leu Arg Leu Ile
GGGATATGTTATGAACGAAAGGGCAGACGAAGAAGGACTCCAAAGAAAACTAAGACTCAT
• • • 6100 • •

Pro Ser Pro Thr Pro Asp Lys
Arg Leu Leu His Gln Thr
Met Met Asn Gln Leu Leu Ile Ala Ile Leu Leu Ala
CCGTCTCCTACACCAGACAAGTGAGTATGATGAATCAGCTGCTTATTGCCATTTTATTAG
• • • • • •

Ser Ala Cys Leu Val Tyr Cys Thr Gln Tyr Val Thr Val Phe Tyr Gly Val Pro Thr Trp
CTAGTGCTTGCTTAGTATATTGCACCCAATATGTAACTGTTTTCTATGGCGTACCCACGT
• 6200 • • • •

Lys Asn Ala Thr Ile Pro Leu Phe Cys Ala Thr Arg Asn Arg Asp Thr Trp Gly Thr Ile
GGAAAAATGCAACCATTCCCCTCTTTTGTGCAACCAGAAATAGGGATACTTGGGGAACCA
• • • • • 6300

Gln Cys Leu Pro Asp Asn Asp Asp Tyr Gln Glu Ile Thr Leu Asn Val Thr Glu Ala Phe
TACAGTGCTTGCCTGACAATGATGATTATCAGGAAATAACTTTGAATGTAACAGAGGCTT
• • • • • •

Asp Ala Trp Asn Asn Thr Val Thr Glu Gln Ala Ile Glu Asp Val Trp His Leu Phe Glu
TTGATGCATGGAATAATACAGTAACAGAACAAGCAATAGAAGATGTCTGGCATCTATTCG
• • • 6400 • •

Thr Ser Ile Lys Pro Cys Val Lys Leu Thr Pro Leu Cys Val Ala Met Lys Cys Ser Ser
AGACATCAATAAAACCATGTGTCAAACTAACACCTTTATGTGTAGCAATGAAATGCAGCA
• • • • • •

Thr Glu Ser Ser Thr Gly Asn Asn Thr Thr Ser Lys Ser Thr Ser Thr Thr Thr Thr Thr
GCACAGAGAGCAGCACAGGGAACAACACAACCTCAAAGAGCACAAGCACAACCACAACCA
• 6500 • • • •

Pro Thr Asp Gln Glu Gln Glu Ile Ser Glu Asp Thr Pro Cys Ala Arg Ala Asp Asn Cys
CACCCACAGACCAGGAGCAAGAGATAAGTGAGGATACTCCATGCGCACGCGCAGACAACT
• • • • • 6600

Ser Gly Leu Gly Glu Glu Glu Thr Ile Asn Cys Gln Phe Asn Met Thr Gly Leu Glu Arg
GCTCAGGATTGGGAGAGGAAGAAACGATCAATTGCCAGTTCAATATGACAGGATTAGAAA
• • • • • •

Asp Lys Lys Lys Gln Tyr Asn Glu Thr Trp Tyr Ser Lys Asp Val Val Cys Glu Thr Asn
GAGATAAGAAAAAACAGTATAATGAAACATGGTACTCAAAAGATGTGGTTTGTGAGACAA
• • • 6700 • •

-continued

Asn Ser Thr Asn Gln Thr Gln Cys Tyr Met Asn His Cys Asn Thr Ser Val Ile Thr Glu
ATAATAGCACAAATCAGACCCAGTGTTACATGAACCATTGCAACACATCAGTCATCACAG

Ser Cys Asp Lys His Tyr Trp Asp Ala Ile Arg Phe Arg Tyr Cys Ala Pro Pro Gly Tyr
AATCATGTGACAAGCACTATTGGGATGCTATAAGGTTTAGATACTGTGCACCACCGGGTT
6800

Ala Leu Leu Arg Cys Asn Asp Thr Asn Tyr Ser Gly Phe Ala Pro Asn Cys Ser Lys Val
ATGCCCTATTAAGATGTAATGATACCAATTATTCAGGCTTTGCACCCAACTGTTCTAAAG
6900

Val Ala Ser Thr Cys Thr Arg Met Met Glu Thr Gln Thr Ser Thr Trp Phe Gly Phe Asn
TAGTAGCTTCTACATGCACCAGGATGATGGAAACGCAAACTTCCACATGGTTTGGCTTTA

Gly Thr Arg Ala Glu Asn Arg Thr Tyr Ile Tyr Trp His Gly Arg Asp Asn Arg Thr Ile
ATGGCACTAGAGCAGAGAATAGAACATATATCTATTGGCATGGCAGAGATAATAGAACTA
7000

Ile Ser Leu Asn Lys Tyr Tyr Asn Leu Ser Leu His Cys Lys Arg Pro Gly Asn Lys Thr
TCATCAGCTTAAACAAATATTATAATCTCAGTTTGCATTGTAAGAGGCCAGGGAATAAGA

Val Lys Gln Ile Met Leu Met Ser Gly His Val Phe His Ser His Tyr Gln Pro Ile Asn
CAGTGAAACAAATAATGCTTATGTCAGGACATGTGTTTCACTCCCACTACCAGCCGATCA
7100

Lys Arg Pro Arg Gln Ala Trp Cys Trp Phe Lys Gly Lys Trp Lys Asp Ala Met Gln Glu
ATAAAAGACCCAGACAAGCATGGTGCTGGTTCAAAGGCAAATGGAAAGACGCCATGCAGG
7200

Val Lys Glu Thr Leu Ala Lys His Pro Arg Tyr Arg Gly Thr Asn Asp Thr Arg Asn Ile
AGGTGAAGGAAACCCTTGCAAAACATCCCAGGTATAGAGGAACCAATGACACAAGGAATA

Ser Phe Ala Ala Pro Gly Lys Gly Ser Asp Pro Glu Val Ala Tyr Met Trp Thr Asn Cys
TTAGCTTTGCAGCGCCAGGAAAAGGCTCAGACCCAGAAGTAGCATACATGTGGACTAACT
7300

Arg Gly Glu Phe Leu Tyr Cys Asn Met Thr Trp Phe Leu Asn Trp Ile Glu Asn Lys Thr
GCAGAGGAGAGTTTCTCTACTGCAACATGACTTGGTTCCTCAATTGGATAGAGAATAAGA

His Arg Asn Tyr Ala Pro Cys His Ile Lys Gln Ile Ile Asn Thr Trp His Lys Val Gly
CACACCGCAATTATGCACCGTGCCATATAAAGCAAATAATTAACACATGGCATAAGGTAG
7400

Arg Asn Val Tyr Leu Pro Pro Arg Glu Gly Glu Leu Ser Cys Asn Ser Thr Val Thr Ser
GGAGAAATGTATATTTGCCTCCCAGGGAAGGGGAGCTGTCCTGCAACTCAACAGTAACCA
7500

Ile Ile Ala Asn Ile Asp Trp Gln Asn Asn Asn Gln Thr Asn Ile Thr Phe Ser Ala Glu
GCATAATTGCTAACATTGACTGGCAAAACAATAATCAGACAAACATTACCTTTAGTGCAG

Val Ala Glu Leu Tyr Arg Leu Glu Leu Gly Asp Tyr Lys Leu Val Glu Ile Thr Pro Ile
AGGTGGCAGAACTATACAGATTGGAGTTGGGAGATTATAAATTGGTAGAAATAACACCAA
7600

Gly Phe Ala Pro Thr Lys Glu Lys Arg Tyr Ser Ser Ala His Gly Arg His Thr Arg Gly
TTGGCTTCGCACCTACAAAAGAAAAAAGATACTCCTCTGCTCACGGGAGACATACAAGAG

Val Phe Val Leu Gly Phe Leu Gly Phe Leu Ala Thr Ala Gly Ser Ala Met Gly Ala Ala
GTGTGTTCGTGCTAGGGTTCTTGGGTTTTCTCGCAACAGCAGGTTCTGCAATGGGCGCGG
7700

Ser Leu Thr Val Ser Ala Gln Ser Arg Thr Leu Leu Ala Gly Ile Val Gln Gln Gln Gln
CGTCCCTGACCGTGTCCGCTCAGTCCCGGACTTTACTGGCCGGGATAGTGCAGCAACAGC
7800

Gln Leu Leu Asp Val Val Lys Arg Gln Gln Glu Leu Leu Arg Leu Thr Val Trp Gly Thr
AACAGCTGTTGGACGTGGTCAAGAGACAACAAGAACTGTTGCGACTGACCGTCTGGGGAA

Lys Asn Leu Gln Ala Arg Val Thr Ala Ile Glu Lys Tyr Leu Gln Asp Gln Ala Arg Leu
CGAAAAACCTCCAGGCAAGAGTCACTGCTATAGAGAAGTACCTACAGGACCAGGCGCGGC
7900

Asn Ser Trp Gly Cys Ala Phe Arg Gln Val Cys His Thr Thr Val Pro Trp Val Asn Asp
TAAATTCATGGGGATGTGCGTTTAGACAAGTCTGCCACACTACTGTACCATGGGTTAATG

Ser Leu Ala Pro Asp Trp Asp Asn Met Thr Trp Gln Glu Trp Glu Lys Gln Val Arg Tyr
ATTCCTTAGCACCTGACTGGGACAATATGACGTGGCAGGAATGGGAAAAACAAGTCCGCT
8000

Leu Glu Ala Asn Ile Ser Lys Ser Leu Glu Gln Ala Gln Ile Gln Gln Glu Lys Asn Met
ACCTGGAGGCAAATATCAGTAAAAGTTTAGAACAGGCACAAATTCAGCAAGAGAAAAATA
8100

Tyr Glu Leu Gln Lys Leu Asn Ser Trp Asp Ile Phe Gly Asn Trp Phe Asp Leu Thr Ser
TGTATGAACTACAAAAATTAAATAGCTGGGATATTTTTGGCAATTGGTTTGACTTAACCT

Trp Val Lys Tyr Ile Gln Tyr Gly Val Leu Ile Ile Val Ala Val Ile Ala Leu Arg Ile
CCTGGGTCAAGTATATTCAATATGGAGTGCTTATAATAGTAGCAGTAATAGCTTTAAGAA
8200

Val Ile Tyr Val Val Gln Met Leu Ser Arg Leu Arg Lys Gly Tyr Arg Pro Val Phe Ser
TAGTGATATATGTAGTACAAATGTTAAGTAGGCTTAGAAAGGGCTATAGGCCTGTTTTCT

Ser Ile Ser Thr Arg Thr Gly Asp Ser Gln Pro
Asn Pro Tyr Pro Gln Gly Pro Gly Thr Ala Ser Gln
Ser Pro Pro Gly Tyr Ile Gln Gln Ile His Ile His Lys Asp Arg Gly Gln Pro Ala Asn
CTTCCCCCCCCGGTTATATCCAACAGATCCATATCCACAAGGACCGGGGACAGCCAGCCA
8300

-continued

Thr Lys Lys Gln Lys Lys Thr Val Glu Ala Thr Val Glu Thr Asp Thr Gly Pro Gly Arg
Arg Arg Asn Arg Arg Arg Arg Trp Lys Gln Arg Trp Arg Gln Ile Leu Ala Leu Ala Asp
Glu Glu Thr Glu Glu Asp Gly Gly Ser Asn Gly Gly Asp Arg Tyr Trp Pro Trp Pro Ile
ACGAAGAAACAGAAGAAGACGGTGGAAGCAACGGTGGAGACAGATACTGGCCCTGGCCGA
• • • • • 8400
Ser Ile Tyr Thr Phe Pro Asp Pro Pro Ala Asp Ser Pro Leu Asp Gln Thr Ile Gln His
Ala Tyr Ile His Phe Leu Ile Arg Gln Leu Ile Arg Leu Leu Thr Arg Leu Tyr Ser Ile
TAGCATATATACATTTCCTGATCCGCCAGCTGATTCGCCTCTTGACCAGACTATACAGCA
• • • • • •
Leu Gln Gly Leu Thr Ile Gln Glu Leu Pro Asp Pro Pro Thr His Leu Pro Glu Ser Gln
Cys Arg Asp Leu Leu Ser Arg Ser Phe Leu Thr Leu Gln Leu Ile Tyr Gln Asn Leu Arg
TCTGCAGGGACTTACTATCCAGGAGCTTCCTGACCCTCCAACTCATCTACCAGAATCTCA
• • • 8500 • •
Arg Leu Ala Glu Thr Met Gly Ala Ser Gly Ser Lys Lys
Asp Trp Leu Arg Leu Arg Thr Ala Phe Leu Gln Tyr Gly Cys Glu Trp Ile Gln Glu Ala
GAGACTGGCTGAGACTTAGAACAGCCTTCTTGCAATATGGGTGCGAGTGGATCCAAGAAG
• • • • • •
His Ser Arg Pro Pro Arg Gly Leu Gln Glu Arg Leu Leu Arg Ala Arg Ala Gly Ala Cys
Phe Gln Ala Ala Ala Arg Ala Thr Arg Glu Thr Leu Ala Gly Ala Cys Arg Gly Leu Trp
CATTCCAGGCCGCCGCGAGGGCTACAAGAGAGACTCTTGCGGGCGCGTGCAGGGGCTTGT
• 8600 • • • •
Gly Gly Tyr Trp Asn Glu Ser Gly Gly Glu Tyr Ser Arg Phe Gln Glu Gly Ser Asp Arg
Arg Val Leu Glu Arg Ile Gly Arg Gly Ile Leu Ala Val Pro Arg Arg Ile Arg Gln Gly
GGAGGGTATTGGAACGAATCGGGAGGGGAATACTCGCGGTTCCAAGAAGGATCAGACAGG
• • • • • 8700
Glu Gln Lys Ser Pro Ser Cys Glu Gly Arg Gln Tyr Gln Gln Gly Asp Phe Met Asn Thr
Ala Glu Ile Ala Leu Leu
GAGCAGAAATCGCCCTCCTGTGAGGGACGGCAGTATCAGCAGGGAGACTTTATGAATACT
• • • • • •
Pro Trp Lys Asp Pro Ala Ala Glu Arg Glu Lys Asn Leu Tyr Arg Gln Gln Asn Met Asp
CCATGGAAGGACCCAGCAGCAGAAAGGGAGAAAAATTTGTACAGGCAACAAAATATGGAT
• • • 8800 • •
Asp Val Asp Ser Asp Asp Asp Asp Gln Val Arg Val Ser Val Thr Pro Lys Val Pro Leu
GATGTAGATTCAGATGATGATGACCAAGTAAGAGTTTCTGTCACACCAAAAGTACCACTA
• • • • • •
Arg Pro Met Thr His Arg Leu Ala Ile Asp Met Ser His Leu Ile Lys Thr Arg Gly Gly
AGACCAATGACACATAGATTGGCAATAGATATGTCACATTTAATAAAAACAAGGGGGGGA
• 8900 • • • •
Leu Glu Gly Met Phe Tyr Ser Glu Arg Arg His Lys Ile Leu Asn Ile Tyr Leu Glu Lys
CTGGAAGGGATGTTTTACAGTGAAAGAAGACATAAAATCTTAAATATATACTTAGAAAAG
• • • • • 9000
Glu Glu Gly Ile Ile Ala Asp Trp Gln Asn Tyr Thr His Gly Pro Gly Val Arg Tyr Pro
GAAGAAGGGATAATTGCAGATTGGCAGAACTACACTCATGGGCCAGGAGTAAGATACCCA
• • • • • •
Met Phe Phe Gly Trp Leu Trp Lys Leu Val Pro Val Asp Val Pro Gln Glu Gly Glu Asp
ATGTTCTTTGGGTGGCTATGGAAGCTAGTACCAGTAGATGTCCCACAAGAAGGGGAGGAC
• • • 9100 • •
Thr Glu Thr His Cys Leu Val His Pro Ala Gln Thr Ser Lys Phe Asp Asp Pro His Gly
ACTGAGACTCACTGCTTAGTACATCCAGCACAAACAAGCAAGTTTGATGACCCGCATGGG
• • • • • •
Glu Thr Leu Val Trp Glu Phe Asp Pro Leu Leu Ala Tyr Ser Tyr Glu Ala Phe Ile Arg
GAGACACTAGTCTGGGAGTTTGATCCCTTGCTGGCTTATAGTTACGAGGCTTTTATTCGG
• 9200 • • • •
Tyr Pro Glu Glu Phe Gly His Lys Ser Gly Leu Pro Glu Glu Glu Trp Lys Ala Arg Leu
TACCCAGAGGAATTTGGGCACAAGTCAGGCCTGCCAGAGGAAGAGTGGAAGGCGAGACTG
• • • • • 9300
Lys Ala Arg Gly Ile Pro Phe Ser
AAAGCAAGAGGAATACCATTTAGTTAAAGACAGGAACAGCTATACTTGGTCAGGGCAGGA
• • • • • •
AGTAACTAACAGAAACAGCTGAGACTGCAGGGACTTTCCAGAAGGGGCTGTAACCAAGGG
• • • 9400 • •
AGGGACATGGGAGGAGCTGGTGGGGAACGCCCTCATATTCTCTGTATAAATATACCCGCT
• • • • • •
AGCTTGCATTGTACTTCGGTCGCTCTGCGGAGAGGCTGGCAGATTGAGCCCTGGGAGGTT
• 9500 • • • •
CTCTCCAGCAGTAGCAGGTAGAGCCTGGGTGTTCCCTGCTAGACTCTCACCAGCACTTGG
• • • • • 9600
CCGGTGCTGGGCAGACGGCCCCACGCTTGCTTGCTTAAAAACCTCCTTAATAAAGCTGCC
• • • • • •
AGTTAGAAGCA
•

Example 5

Sequences of the Coding Regions for the Envelope Protein and GAG Product of the ROD HIV-2 Isolate Through experimental analysis of the HIV-2 ROD isolate, the following sequences were identified for the regions encoding the env and gag gene products. One of the ordinary skill in the art will recognize that the numbering for both gene regions which follow begins for convenience with “1” rather than the corresponding number for its initial nucleotide as given in Example 4, above, in the context of the complete genomic sequence.

Envelope sequence

Met Met Asn Gln Leu Leu Ile Ala Ile Leu Leu Als Ser Ala Cys
ATGATGAATCAGCTGCTTATTGCCATTTTATTAGCTAGTGCTTGC

Leu Val Tyr Cys Thr Gln Tyr Val Thr Val Phe Tyr Gly Val Pro
TTAGTATATTGCACCCAATATGTAACTGTTTTCTATGGCGTACCC

Thr Trp Lys Asn Ala Thr Ile Pro Leu Phe Cys Ala Thr Arg Asn
ACGTGGAAAAATGCAACCATTCCCCTGTTTTGTGCAACCAGAAAT
100

Arg Asp Thr Trp Gly Thr Ile Gln Cys Leu Pro Asp Asn Asp Asp
AGGGATACTTGGGGAACCATACAGTGCTTGCCTGACAATGATGAT

Tyr Gln Glu Ile Thr Leu Asn Val Thr Glu Ala Phe Asp Ala Trp
TATCAGGAAATAACTTTGAATGTAACAGAGGCTTTTGATGCATGG
200

Asn Asn Thr Val Thr Glu Gln Ala Ile Glu Asp Val Trp His Leu
AATAATACAGTAACAGAACAAGCAATAGAAGATGTCTGGCATCTA

Phe Glu Thr Ser Ile Lys Pro Cys Val Lys Leu Thr Pro Leu Cys
TTCGAGACATCAATAAAACCATGTGTGAAACTAACACCTTTATGT
300

Val Ala Met Lys Cys Ser Ser Thr Glu Ser Ser Thr Gly Asn Asn
GTAGCAATGAAATGCAGCAGCACAGAGAGCAGCACAGGGAACAAC

Thr Thr Ser Lys Ser Thr Ser Thr Thr Thr Thr Thr Pro Thr Asp
ACAACCTCAAAGAGCACAAGCACAACCACAACCACACCCAGAGAC
400

Gln Glu Gln Glu Ile Ser Glu Asp Thr Pro Cys Ala Arg Ala Asp
CAGGAGCAAGAGATAAGTGAGGATACTCCATGCGCACGCGCAGAC

Asn Cys Ser Gly Leu Gly Glu Glu Glu Thr Ile Asn Cys Gln Phe
AACTGCTCAGGATTGGGAGAGGAAGAAACGATCAATTGCCAGTTC

Asn Met Thr Gly Leu Glu Arg Asp Lys Lys Lys Gln Tyr Asn Glu
AATATGACAGGATTAGAAAGAGATAAGAAAAAACAGTATAATGAA
500

Thr Trp Tyr Ser Lys Asp Val Val Cys Glu Thr Asn Asn Ser Thr
ACATGGTACTCAAAAGATGTGGTTTGTGAGACAAATAATAGCACA

Asn Gln Thr Gln Cys Tyr Met Asn His Cys Asn Thr Ser Val Ile
AATCAGACCCAGTGTTACATGAACCATTGCAACACATCAGTCATC
600

Thr Glu Ser Cys Asp Lys His Tyr Trp Asp Ala Ile Arg Phe Arg
ACAGAATCATGTGACAAGCACTATTGGGATGCTATAAGGTTTAGA

Tyr Cys Ala Pro Pro Gly Tyr Ala Leu Leu Arg Cys Asn Asp Thr
TACTGTGCACCACCGGGTTATGCCCTATTAAGATGTAATGATACC
700

Asn Tyr Ser Gly Phe Ala Pro Asn Cys Ser Lys Val Val Ala Ser
AATTATTCAGGCTTTGCACCCAACTGTTCTAAAGTAGTAGCTTCT

Thr Cys Thr Arg Met Met Glu Thr Gln Thr Ser Thr Trp Phe Gly
ACATGCACCAGGATGATGGAAACGCAAAGTTCCACATGGTTTGGC
800

Phe Asn Gly Thr Arg Ala Glu Asn Arg Thr Tyr Ile Tyr Trp His
TTTAATGGCACTAGAGCAGAGAATAGAACATATATCTATTGGCAT

Gly Arg Asp Asn Arg Thr Ile Ile Ser Leu Asn Lys Tyr Tyr Asn
GGCAGAGATAATAGAACTATCATCAGCTTAAACAAATATTATAAT
900

Leu Ser Leu His Cys Lys Arg Pro Gly Asn Lys Thr Val Lys Gln
CTCAGTTTGCATTGTAAGAGGCCAGGGAATAAGACAGTGAAACAA

Ile Met Leu Met Ser Gly His Val Phe His Ser His Tyr Gln Pro
ATAATGCTTATGTCAGGACATGTGTTTCACTCCCACTACCAGCCG

Ile Asn Lys Arg Pro Arg Gln Ala Trp Cys Trp Phe Lys Gly Lys
ATCAATAAAAGACCCAGACAAGCATGGTGCTGGTTCAAAGGCAAA
1000

Trp Lys Asn Ala Met Gln Glu Val Lys Thr Leu Ala Lys His Pro
TGGAAAGACGCCATGCAGGAGGTGAAGACCCTTGCAAAACATCCC

Arg Tyr Arg Gly Thr Asn Asp Thr Arg Asn Ile Ser Phe Ala Ala
AGGTATAGAGGAACCAATGACACAAGGAATATTAGCTTTGCAGCG
1100

Pro Gly Lys Gly Ser Asp Pro Glu Val Ala Tyr Met Trp Thr Asn
CCAGGAAAAGGCTCAGACCCAGAAGTAGCATACATGTGGACTAAC

Cys Arg Gly Glu Phe Leu Tyr Cys Asn Met Thr Trp Phe Leu Asn
TGCAGAGGAGAGTTTCTCTACTGCAACATGACTTGGTTCCTCAAT
1200

-continued

Trp Ile Glu Asn Lys Thr His Arg Asn Tyr Ala Pro Cys His Ile
TGGATAGAGAATAAGACACACCGCAATTATGCACCGTGCCATATA

Lys Gln Ile Ile Asn Thr Trp His Lys Val Gly Arg Asn Val Tyr
AAGCAAATAATTAACACATGGCATAAGGTAGGGAGAAATGTATAT
1300

Leu Pro Pro Arg Glu Gly Glu Leu Ser Cys Asn Ser Thr Val Thr
TTGCCTCCCAGGGAACGGGAGCTGTCCTGCAACTCAACAGTAACC

Ser Ile Ile Ala Asn Ile Asp Trp Gln Asn Asn Asn Gln Thr Asn
AGCATAATTGCTAACATTGACTGGCAAAACAATAATCAGACAAAC

Ile Thr Phe Ser Ala Glu Val Ala Glu Leu Tyr Arg Leu Glu Leu
ATTACCTTTAGTGCAGAGGTGGCAGAACTATACAGATTGGAGTTG
1400

Gly Asp Tyr Lys Leu Val Glu Ile Thr Pro Ile Gly Phe Ala Pro
GGAGATTATAAATTGGTAGAAATAACACCAATTGGCTTCGCACCT

Thr Lys Glu Lys Arg Tyr Ser Ser Ala His Gly Arg His Thr Arg
ACAAAAGAAAAAAGATACTCCTCTGCTCACGGGAGACATACAAGA
1500

Gly Val Phe Val Leu Gly Phe Leu Gly Phe Leu Ala Thr Ala Gly
GGTGTGTTCGTGCTAGGGTTCTTGGGTTTTCTCGCAACAGCAGGT

Ser Ala Met Gly Ala Arg Ala Ser Leu Thr Val Ser Ala Gln Ser
TCTGCAATGGGCGCTCGAGCGTCCCTGACCGTGTCGGCTCAGTCC
1600

Arg Thr Leu Leu Ala Gly Ile Val Gln Gln Gln Gln Gln Leu Leu
CGGACTTTACTGGCCGGGATAGTGCAGCAACAGCAACAGCTGTTG

Asp Val Val Lys Arg Gln Gln Glu Leu Leu Arg Leu Thr Val Trp
GACGTGGTCAAGAGACAACAAGAACTGTTGCGACTGACCGTCTGG
1700

Gly Thr Lys Asn Leu Gln Ala Arg Val Thr Ala Ile Glu Lys Tyr
GGAACGAAAAACCTCCAGGCAAGAGTCACTGCTATAGAGAAGTAG

Leu Glu Asp Gln Ala Arg Leu Asn Ser Trp Gly Cys Ala Phe Arg
CTACAGGACCAGGCGCGGCTAAATTCATGGGGATGTGCGTTTAGA
1800

Gln Val Cys His Thr Thr Val Pro Trp Val Asn Asp Ser Leu Ala
CAAGTCTGCCACACTACTGTACCATGGGTTAATGATTCCTTAGCA

Pro Asp Trp Asp Asn Met Thr Trp Gln Glu Trp Glu Lys Glu Val
CCTGACTGGGACAATATGACGTGGCAGGAATGGGAAAAACAAGTC

Arg Tyr Leu Glu Ala Asn Ile Ser Lys Ser Leu Glu Gln Ala Gln
CGCTACCTGGAGGCAAATATCAGTAAAAGTTTAGAACAGGCACAA
1900

Ile Gln Gln Glu Lys Asn Met Tyr Glu Leu Gln Lys Leu Asn Ser
ATTCAGCAAGAGAAAAATATGTATGAACTACAAAAATTAAATAGC

Trp Asp Ile Phe Gly Asn Trp Phe Asp Leu Thr Ser Trp Val Lys
TGGGATATTTTTGGCAATTGGTTTGACTTAACCTCCTGGGTCAAG
2000

Tyr Ile Gln Tyr Gly Val Leu Ile Ile Val Ala Val Ile Ala Leu
TATATTCAATATGGAGTGCTTATAATAGTAGCAGTAATAGCTTTA

Arg Ile Val Ile Tyr Val Val Gln Met Leu Ser Arg Leu Arg Lys
AGAATAGTGATATATGTAGTACAAATGTTAAGTAGGCTTAGAAAG
2100

Gly Tyr Arg Pro Val Phe Ser Ser Pro Pro Gly Tyr Ile Gln ***
GGCTATAGGCCTGTTTTCTCTTCCCCCCCGGTTATATCCAATAG

Ile His Ile His Lys Asp Arg Gly Gln Pro Ala Asn Glu Glu Thr
ATCCATATCCACAAGGACCGGGGACAGCCAGCCAACGAAGAAACA
2200

Glu Glu Asp Gly Gly Ser Asn Gly Gly Asp Arg Tyr Trp Pro Trp
GAAGAAGACGGTGGAAGCAACGGTGGAGACAGATACTGGCCCTGG

Pro Ile Ala Tyr Ile His Phe Leu Ile Arg Gln Leu Ile Arg Leu
GCGATAGCATATATACATTTCCTGATCCGCCAGCTGATTCGCCTC

Leu Thr Arg Leu Tyr Ser Ile Cys Arg Asp Leu Leu Ser Arg Ser
TTGACCAGACTATACAGCATCTGCAGGGACTTACTATCCAGGAGC
2300

Phe Leu Thr Leu Gln Leu Ile Tyr Gln Asn Leu Arg Asp Trp Leu
TTCCTGACCCTCCAACTCATCTACCAGAATCTCAGAGACTGGCTG

Arg Leu Arg Thr Ala Phe Leu Gln Tyr Gly Cys Glu Trp Ile Gln
AGACTTAGAACAGCCTTCTTGCAATATGGGTGCGAGTGGATCCAA
2400

Glu Ala Phe Gln Ala Ala Ala Arg Ala Thr Arg Glu Thr Leu Ala
GAAGCATTCCAGGCCGCCGCGAGGGCTACAAGAGAGACTCTTGCG

-continued

Gly Ala Cys Arg Gly Leu Trp Arg Val Leu Glu Arg Ile Gly Arg
GGCGCGTGCAGGGGCTTGTGGAGGGTATTGGAACGAATCGGGAGG

2500

Gly Ile Leu Ala Val Pro Arg Arg Ile Arg Gln Gly Ala Glu Ile
GGAATACTCGCGGTTCCAAGAAGGATCAGACAGGGAGCAGAAATC

Ala Leu Leu *** Gly Thr Ala Val Ser Ala Gly Arg Leu Tyr Glu
GCCCTCCTGTGAGGGACGGCAGTATCAGCAGGGAGACTTTATGAA

2600

Tyr Ser Met Glu Gly Pro Ser Ser Arg Lys Gly Glu Lys Phe Val
TACTCCATGGAAGGACCCAGCAGCAGAAAGGGAGAAAAATTTGTA

Gln Ala Thr Lys Tyr Gly
CAGGCAACAAAATATGGA

Gag sequence

Met Gly Ala Arg Asn Ser Val Leu Arg Gly Lys Lys Ala Asp Glu
ATGGGCGCGAGAAACTCCGTCTTGAGAGGGAAAAAAGCAGATGAA

Leu Glu Arg Ile Arg Leu Arg Pro Gly Gly Lys Lys Lys Tyr Arg
TTAGAAAGAATCAGGTTACGGCCCGGCGGAAAGAAAAAGTACAGG

Leu Lys His Ile Val Trp Ala Ala Asn Lys Leu Asp Arg Phe Gly
CTAAAACATATTGTGTGGGCAGCGAATAAATTGGACAGATTCGGA

100

Leu Ala Glu Ser Leu Leu Glu Ser Lys Glu Gly Cys Gln Lys Ile
TTAGCAGAGAGCCTGTTGGAGTCAAAAGAGGGTTGTCAAAAAATT

Leu Thr Val Leu Asp Pro Met Val Pro Thr Gly Ser Glu Asn Leu
CTTACAGTTTTAGATCCAATGGTACCGACAGGTTCAGAAAATTTA

200

Lys Ser Leu Phe Asn Thr Val Cys Val Ile Trp Cys Ile His Ala
AAAAGTCTTTTTAATACTGTCTGCGTCATTTGGTGCATACACGCA

Glu Glu Lys Val Lys Asp Thr Glu Gly Ala Lys Gln Ile Val Arg
GAAGAGAAAGTGAAAGATACTGAAGGAGCAAAACAAATAGTGCGG

300

Arg His Leu Val Ala Glu Thr Gly Thr Ala Glu Lys Met Pro Ser
AGACATCTAGTGGCAGAAACAGGAACTGCAGAGAAAATGCCAAGC

Thr Ser Arg Pro Thr Ala Pro Ser Ser Glu Lys Gly Gly Asn Tyr
ACAAGTAGACCAACAGCACCATCTAGCGAGAAGGGAGGAAATTAC

400

Pro Val Gln His Val Gly Gly Asn Tyr Thr His Ile Pro Leu Ser
CCAGTGCAACATGTAGGCGGCAACTACACCCATATACCGCTGAGT

Pro Arg Thr Leu Asn Ala Trp Val Lys Leu Val Glu Glu Lys Lys
CCCCGAACCCTAAATGCCTGGGTAAAATTAGTAGAAGAAAAAAAG

Phe Gly Ala Glu Val Val Pro Gly Phe Gln Ala Leu Ser Glu Gly
TTCGGGGCAGAAGTAGTGCCAGGATTTCAGGCACTCTCAGAAGGC

500

Cys Thr Pro Tyr Asp Ile Asn Gln Met Leu Asn Cys Val Gly Asp
TGCACGCCCTATGATATCAACCAAATGCTTAATTGTGTGGGCGAC

His Gln Ala Ala Met Gln Ile Ile Arg Glu Ile Ile Asn Glu Glu
CATCAAGCAGCCATGCAGATAATCAGGGAGATTATCAATGAGGAA

600

Ala Ala Glu Trp Asp Val Gln His Pro Ile Pro Gly Pro Leu Pro
GCAGCAGAATGGGATGTGCAACATCCAATACCAGGCCCCTTACCA

Ala Gly Gln Leu Arg Glu Pro Arg Gly Ser Asp Ile Ala Gly Thr
GCGGGGCAGCTTAGAGAGCCAAGGGGATCTGACATAGCAGGGACA

-continued

Gag sequence

```
                                   700
Thr Ser Thr Val Glu Glu Gln Ile Gln Trp Met Phe Arg Pro Gln
ACAAGCACAGTAGAAGAACAGATCCAGTGGATGTTTAGGCCACA

Asn Pro Val Pro Val Gly Asn Ile Tyr Arg Arg Trp Ile Gln Ile
AATCCTGTACCAGTAGGAAACATCTATAGAAGATGGATCCAGATA

                                           800
Gly Leu Gln Lys Cys Val Arg Met Tyr Asn Pro Thr Asn Ile Leu
GGATTGCAGAAGTGTGTCAGGATGTACAACCCGACCAACATCCTA

Asp Ile Lys Gln Gly Pro Lys Glu Pro Phe Gln Ser Tyr Val Asp
GACATAAAACAGGGACCAAAGGAGCCGTTCCAAAGCTATGTAGAT

                                                       900
Arg Phe Tyr Lys Ser Leu Arg Ala Glu Gln Thr Asp Pro Ala Val
AGATTCTACAAAAGCTTGAGGGCAGAAGAAACAGATCCAGCAGTG

Lys Asn Trp Met Thr Gln Thr Leu Leu Val Gln Asn Ala Asn Pro
AAGAATTGGATGACCCAAACACTGCTAGTACAAAATGCCAACGCA

Asp Cys Lys Leu Val Leu Lys Gly Leu Gly Met Asn Pro Thr Leu
GACTGTAAATTAGTGCTAAAAGGACTAGGGATGAACCCTACCTTA

        1000
Glu Glu Met Leu Thr Ala Cys Gln Gly Val Gly Gly Pro Gly Gln
GAAGAGATGCTGACCGCCTGTCAGGGGGTAGGTGGGCCAGGCCAG

Lys Ala Arg Leu Met Ala Glu Ala Leu Lys Glu Val Ile Gly Pro
AAAGCTAGATTAATGGCAGAGGCCCTGAAAGAGGTCATAGGACCT

                     1100
Ala Pro Ile Pro Phe Ala Ala Ala Gln Gln Arg Lys Ala Phe Lys
GCCCCTATCCCATTCGCAGCAGCCCAGCAGAGAAAGGCATTTAAA

Cys Trp Asn Cys Gly Lys Glu Gly His Ser Ala Arg Gln Cys Arg
TGCTGGAACTGTGGAAAGGAAGGGCACTCGGCAAGACAATGCCGA

                                   1200
Ala Pro Arg Arg Gln Gly Cys Trp Lys Cys Gly Lys Pro Gly His
GCACCTAGAAGGCAGGGCTGCTGGAAGTGTGGTAAGCCAGGACAC

Ile Met Thr Asn Cys Pro Asp Arg Gln Ala Gly Phe Leu Gly Leu
ATCATGACAAACTGCCCAGATAGACAGGCAGGTTTTTTAGGACTG

                                               1300
Gly Pro Trp Gly Lys Lys Pro Arg Asn Phe Pro Val Ala Gln Val
GGCCCTTGGGGAAAGAAGCCCCGCAACTTCCCCGTGGCCCAAGTT

Pro Gln Gly Leu Thr Pro Thr Ala Pro Pro Val Asp Pro Ala Val
CCGCAGGGGCTGACACCAACAGCACCCCCAGTGGATCCAGCAGTG

Asp Leu Leu Glu Lys Tyr Het Gln Gln Gly Lys Arg Gln Arg Glu
GATCTACTGGAGAAATATATGCAGCAAGGGAAAAGACAGAGAGAG

1400
Gln Arg Glu Arg Pro Tyr Lys Glu Val Thr Glu Asp Leu Leu His
CAGAGAGAGAGACCATACAAGGAAGTGACAGAGGACTTACTGCAC

Leu Glu Gln Gly Glu Thr Pro Tyr Arg Glu Pro Pro Thr Glu Asp
CTCGAGCAGGGGGAGACACCATACAGGGAGCCACCAACAGAGGAG

            1500
Leu Leu His Leu Asn Ser Leu Phe Gly Lys Asp Gln
TTGCTGCACCTCAATTCTCTCTTTGGAAAAGACCAG
```

Example 6

Peptide Sequences Encoded by the ENV and GAG Genes

The following coding regions for antigenic peptides, identified for convenience only by the nucleotide numbers of Example 5, within the env and gag gene regions are of particular interest.

envl (1732-1809)
Arg Val Thr Ala Ile Glu Lys Tyr
AGAGTCACTGCTATAGAGAAGTAG

Leu Glu Asp Gln Ala Arg Leu Asn Ser Trp Gly Cys Ala Phe Arg
CTACAGGACCAGGCGCGGCTAAATTCATGGGGATGTGCGTTTAGA
1000
Gln Val Cys
CAAGTCTGC env2 (1912-1983)
Ser Lys Ser Leu Glu Gln Ala Gln
AGTAAAAGTTTAGAACAGGCACAA Ile Gln Gln Glu Lys Asn Met Tyr Glu Leu Gln Lys Leu Asn Ser
ATTCAGCAAGAGAAAAATATGTATGAACTACAAAAATTAAATAGC
1940
Trp
TGG env2 (1482-1530)
Pro Thr Lys Glu Lys Arg Tyr Ser Ser Ala His Gly Arg His Thr Arg
CCTACAAAAGAAAAAAGATACTCCTCTGCTCAGGGGAGACATACAAGA
1500 env4 (55-129)
Cys Thr Gln Tyr Val Thr Val Phe Tyr Gly Val Pro
TGCACCCAATATGTAACTGTTTTCTATGGCGTACCC Thr Trp Lys Asn Ala Thr Ile Pro Leu Phe Cys Ala Thr
ACGTGGAAAAATGCAACCATTCCCCTGTTTTGTGCAACC
100 env5 (175-231)
Asp Asp
GATGAT

Tyr Gln Glu Ile Thr Leu Asn Val Thr Glu Ala Phe Asp Ala Trp
TATGAGGAAATAACTTTGAATGTAACAGAGGCTTTTGATGCATGG
200
Asn Asn
AATAAT env6 (274-330)
Glu Thr Ser Ile Lys Pro Cys Val Lys Leu Thr Pro Leu Cys
GAGACATCAATAAAACCATGTGTGAAACTAACACCTTTATGT
300
Val Ala Met Lys Cys
GTAGCAATGAAATGC env7 (607-660)
Asn His Cys Asn Thr Ser Val Ile
AACCATTGCAACACATCAGTCATC
610
Thr Glu Ser Cys Asp Lys His Tyr Trp Asp
ACAGAATCATGTGACAAGCACTATTGGGAT env8 (661-720)
Ala Ile Arg Phe Arg
GCTATAAGGTTTAGA Tyr Cys Ala Pro Pro Gly Tyr Ala Leu Leu Arg Cys Asn Asp Thr
TACTGTGCACCACGGGGTTATGCCCTATTAAGATGTAATGATACC
700 env9 (997-1044)
Lys Arg Pro Arg Gln Ala Trp Cys Trp Phe Lys Gly Lys
AAAAGACCCAGACAAGCATGGTGCTGGTTCAAAGGCAAA
1000
Trp Lys Asp
TGGAAAGAC env10 (1132-1215)
Lys Gly Ser Asp Pro Glu Val Ala Tyr Met Trp Thr Asn
AAAGGCTCAGACCCAGAAGTAGCATACATGTGGACTAAC Cys Arg Gly Glu Phe Leu Tyr Cys Asn Met Thr Trp Phe Leu Asn
TGCAGAGGAGAGTTTCTCTACTGCAACATGACTTGGTTCCTCAAT
1200

-continued env11 (1237-1305)

```
                                            Arg  Asn  Tyr  Ala  Pro  Cys  His  Ile
                                            CGCAATTATGCACCGTGCCATATA
                                                      .              .          .
Lys  Gln  Ile  Ile  Asn  Thr  Trp  His  Lys  Val  Gly  Arg  Asn  Val  Tyr
AAGCAAATAATTAACACATGGCATAAGGTAGGGAAGAATGTATAT
                  .              .              .            1300
```

gag1 (991-1053)

```
Asp  Cys  Lys  Leu  Val  Leu  Lys  Gly  Leu  Gly  Met  Asn  Pro  Thr  Leu
GACTGTAAATTAGTGCTAAAAGGACTAGCGATGAACCCTACCTTA
          1000                .              .              .

Glu  Glu  Met  Leu  Thr  Ala
GAAGAGATGCTGACCGCC
       .              .
```

Of the foregoing peptides, env1, env2, env3 and gag1 are particularly contemplated for diagnostic purposes, and env4, env5, env6, env7, env8, env9, env10 and env11 are particularly contemplated as protecting agents. These peptides have been selected in part because of their sequence homology to certain of the envelope and gag protein products of other of the retroviruses in the HIV group. For vaccinating purposes, the foregoing peptides may be coupled to a carrier protein by utilizing suitable and well known techniques to enhance the host's immune response. Adjuvants such as calcium phosphate or alum hydroxide may also be added. The foregoing peptides can be synthesized by conventional protein synthesis techniques, such as that of Merrifield.

It will be apparent to those skilled in the art that various modifications and variations can be made in the process and products of the present invention. Thus, it is intended that the present application cover the modifications and variations of this invention provided they come within the scope of the appended claims and their equivalents. For convenience in interpreting the following claims, the following table sets forth the correspondence between codon codes and amino acids and the correspondence between three-letter and one-letter amino acid symbols.

| | \2 | DNA CODON | | | | AMINO ACID 3 LET. | | | | AMINO ACID 1 LET. | | | |
|---|---|---|---|---|---|---|---|---|---|---|---|---|---|
| 1 | 3\ | T | C | A | G | T | C | A | G | T | C | A | G |
| T | T | TTT | TCT | TAT | TGT | PHE | SER | TYR | CYS | F | S | Y | C |
| | C | TTC | TCC | TAC | TGC | PHE | SER | TYR | CYS | F | S | Y | C |
| | A | TTA | TCA | TAA | TGA | LEU | SER | *** | *** | L | S | * | * |
| | G | TTG | TCG | TAG | TGG | LEU | SER | *** | TRP | L | S | * | W |
| C | T | CTT | CCT | CAT | CGT | LEU | PRO | HIS | ARG | L | P | H | R |
| | C | CTC | CCC | CAC | CGC | LEU | PRO | HIS | ARG | L | P | H | R |
| | A | CTA | CCA | CAA | CGA | LEU | PRO | GLN | ARG | L | P | O | R |
| | G | CTG | CCG | CAG | CGG | LEU | PRO | GLN | ARG | L | P | O | R |
| A | T | ATT | ACT | AAT | AGT | ILE | THR | ASN | SER | I | T | N | S |
| | C | ATC | ACC | AAC | AGC | ILE | THR | ASN | SER | I | T | N | S |
| | A | ATA | ACA | AAA | AGA | ILE | THR | LYS | ARG | I | T | K | R |
| | G | ATG | ACG | AAG | AGG | MET | THR | LYS | ARG | M | T | K | R |
| G | T | GTT | GCT | GAT | GGT | VAL | ALA | ASP | GLY | V | A | D | G |
| | C | GTC | GCC | GAC | GGC | VAL | ALA | ASP | GLY | V | A | D | G |
| | A | GTA | GCA | GAA | GGA | VAL | ALA | GLU | GLY | V | A | E | G |
| | G | GTG | GCG | GAG | GGG | VAL | ALA | GLU | GLY | V | A | E | G |

| 3 Letter | 1 Letter | CODONS | | | | | |
|---|---|---|---|---|---|---|---|
| ALA | A | GCT | GCC | GCA | GCG | | |
| ARG | R | CGT | CGC | CGA | CGG | AGA | AGG |
| ASN | N | AAT | AAC | | | | |

-continued

| 3 Letter | 1 Letter | CODONS | | | | | |
|---|---|---|---|---|---|---|---|
| ASP | D | GAT | GAC | | | | |
| CYS | C | TGT | TGC | | | | |
| GLN | O | CAA | CAG | | | | |
| GLU | E | GAA | GAG | | | | |
| GLY | G | GGT | GGC | GGA | GGG | | |
| HIS | H | CAT | CAC | | | | |
| ILE | I | ATT | ATC | ATA | | | |
| LEU | L | CTT | CTC | CTA | CTG | TTA | TTG |
| LYS | K | AAA | AAG | | | | |
| MET | M | ATG | | | | | |
| PHE | F | TTT | TTC | | | | |
| PRO | P | CCT | CCC | CCA | CCG | | |
| SER | S | TCT | TCC | TCA | TCG | AGT | AGC |
| THR | T | ACT | ACC | ACA | ACG | | |
| TRP | W | TGG | | | | | |
| TYR | Y | TAT | TAC | | | | |
| VAL | V | GTT | GTC | GTA | GTG | | |
| *** | * | TAA | TAG | TGA | | | |

What is claimed is:

1. An isolated or purified nucleic acid of HIV-2 capable of encoding for the envelope glycoprotein having the following nucleotide sequence;

```
ATGATGAATCAGCTGCTTATTGCCATTTTATTAGCTAGTGCTTGC
                  .              .              .              .

TTAGTATATTGCACCCAATATGTAACTGTTTTCTATGGCGTACCC
      .              .              .              .              .
```

-continued

ACGTGGAAAAATGCAACCATTCCCCTGTTTTGTGCAACCAGAAAT
100 . . .

AGGGATACTTGGGGAACCATACAGTGCTTGCCTGACAATGATGAT
. . . . .

TATCAGGAAATAACTTTGAATGTAACAGAGGCTTTTGATGCATGG
. 200 . .

AATAATACAGTAACAGAACAAGCAATAGAAGATGTCTGGCATCT
. . . .

ATTCGAGACATCAATAAAACCATGTGTGAAACTAACACCTTTATG
. . 300 .

TGTAGCAATGAAATGCAGCAGCACAGAGAGCAGCACAGGGAACA
. . . .

ACACAACCTCAAAGAGCACAAGCACAACCACAACCACACCCAGA
. . . . 400

GACCAGGAGCAAGAGATAAGTGAGGATACTCCATGCGCACGCGC
. . . .

AGACAACTGCTCAGGATTGGGAGAGGAAGAAACGATCAATTGCC
. . . . .

AGTTCAATATGACAGGATTAGAAAGAGATAAGAAAAAACAGTAT
500 . . .

AATGAAACATGGTACTCAAAAGATGTGGTTTGTGAGACAAATAAT
. . . .

AGCACAAATCAGACCCAGTGTTACATGAACCATTGCAACACATCA
. . 600 . .

GTCATCACAGAATCATGTGACAAGCACTATTGGGATGCTATAAGG
. . . .

TTTAGATACTGTGCACCACCGGGTTATGCCCTATTAAGATGTAAT
. . . 700 .

GATACCAATTATTCAGGCTTTGCACCCAACTGTTCTAAAGTAGTA
. . . .

GCTTCTACATGCACCAGGATGATGGAAACGCAAACTTCCACATGG
. . . . 800

TTTGGCTTTAATGGCACTAGAGCAGAGAATAGAACATATATCTAT
. . . .

TGGCATGGCAGAGATAATAGAACTATCATCAGCTTAAACAAATAT
. . . . .

TATAATCTCAGTTTGCATTGTAAGAGGCCAGGGAATAAGACAGTG
900 . . .

AAACAATAATGCTTATGTCAGGACATGTGTTTCACTCCCACTAC
. . . . .

CAGCCGATCAATAAAAGACCCAGACAAGCATGGTGCTGGTTCAA
. 1000 . .

AGGCAAATGGAAAGACGCCATGCAGGAGGTGAAGACCCTTGCAA
. . . . .

AACATCCCAGGTATAGAGGAACCAATGACACAAGGAATATTAGC
. . 1100 .

TTTGCAGCGCCAGGAAAAGGCTCAGACCCAGAAGTAGCATACA
. . . .

TGTGGACTAACTGCAGAGGAGAGTTTCTCTACTGCAACATGACTT
. . . . 1200

GGTTCCTCAATTGGATAGAGAATAAGACACACCGCAATTATGCAC
. . . .

CGTGCCATATAAAGCAAATAATTAACACATGGCATAAGGTAGGG
. . . . .

AGAAATGTATATTTGCCTCCCAGGGAAGGGGAGCTGTCCTGCAAC
1300 . . .

-continued

TCAACAGTAACCAGCATAATTGCTAACATTGACTGGCAAAAGAAT
. . . . .

AATCAGACAAACATTACCTTTAGTGCAGAGGTGGCAGAACTATAC
. 1400 . .

AGATTGGAGTTGGCAGATTATAAATTGGTAGAAATAACACCAATT
. . . .

GGCTTCGCACCTACAAAAGAAAAAAGATACTCCTCTGCTCACGGG
. . 1500 .

AGACATACAAGAGGTGTGTTCGTGCTAGGGTTCTTGGGTTTTCTCG
. . . . .

CAACAGCAGGTTCTGCAATGGGCGCTCGAGCGTCCCTGACCGTGT
. . . 1600

CGGCTCAGTCCCGGACTTTACTGGCCGGGATAGTGCAGCAACAGC
. . . . .

AACAGCTGTTGGACGTGGTCAAGAGACAACAAGAACTGTTGCGA
. . . . 1700

CTGACCGTCTGGGGAACGAAAAACCTCCAGGCAAGAGTCACTGC
. . . .

TATAGAGAAGTACCTACAGGACCAGGCGCGGCTAAATTCATGGG
. . . .

GATGTGCGTTTAGACAAGTCTGCCACACTACTGTACCATGGGTT
. 1800 . . .

AATGATTCCTTAGCACCTGACTGGGACAATATGACGTGGCAGGA
. . . .

ATGGGAAAAACAAGTCCGCTACCTGGAGGCAAATATCAGTAAAA
. . 1900 .

GTTTAGAACAGGCACAAATTCAGCAAGAGAAAAATATGTATGAA
. . . . .

CTACAAAAATTAAATAGCTGGGATATTTTTGGCAATTGGTTTGACT
. . . 2000

TAACCTCCTGGGTCAAGTATATTCAATATGGAGTGCTTATAATAG
. . . . .

TAGCAGTAATAGCTTTAAGAATAGTGATATATGTAGTACAAATGT
. . . . 2100

TAAGTAGGCTTAGAAAGGGCTATAGGCCTGTTTTCTCTTCCCCCCC
.

CGGTTATATCCAATAGATCCATATCCACAAGGACCGGGGAC
. .

AGCCAGCCAACGAAGAAACAGAAGAAGACGGTGGAAGCAACGG
. 2200 . .

TGGAGACAGATACTGGCCCTGGGCGATAGCATATATACATTTCCT
. . . . .

GATCCGCCAGCTGATTCGCCTCTTGACCAGACTATACAGCATCT
. . 2300 .

GCAGGGACTTACTATCCAGGAGCTTCCTGACCCTCCAACTCATCT
. . . . .

ACCAGAATCTCAGAGACTGGCTGAGACTTAGAACAGCCTTCTTGC
. . . 2400

AATATGGGTGCGAGTGGATCCAAGAAGCATTCCAGGCCGCCGCG
. . . . .

AGGGCTACAAGAGAGACTCTTGCGGGCGCGTGCAGGGGCTTGTG
. . . .

GAGGGTATTGGAACGAATCGGGAGGGGAATACTCGCGGTTCCA
2500 . . .

AGAAGGATCAGACAGGGAGCAGAAATCGCCCTCCTGTGAGGGA
. . . . .

-continued
CGGCAGTATCAGCAGGGAGACTTTATGAATACTCCATGGA
                        2600
AGGACCCAGCAGCAGAAAGGGAGAAAAATTTGTACAGGC

AACAAAATATGGA.

2. An isolated or purified subgenomic HIV-2 nucleic acid capable of encoding for a segment of the envelope glycoprotein, wherein the nucleic acid is selected from the group consisting of:
  a) a nucleic acid, designated env1, having the following nucleotide sequence;
  AGAGTCACTG CTATAGAGAA GTACCTACAG GAC-CAGGCGC GGCTAAATTC ATGGGGATGT GCGTTTA-GAC AAGTCTGC;
  b) a nucleic acid, designated env2, having the following nucleotide sequence;
  AGTAAAAGT TTAGAACAGG CACAAATTCA GCAA-GAGAAA AATATGTATG AACTACAAAA ATTAAAT-AGC TGG;
  c) a nucleic acid, designated env3, having the following nucleotide sequence;
  CCTACAAAA GAAAAAAGAT ACTCCTCTGC TCACGGGAGA CATACAAGA;
  d) a nucleic acid, designated env4, having the following nucleotide sequence;
  TGCACCCAA TATGTAACTG TTTTCTATGG CGTAC-CCACG TGGAAAAATG CAACCATTCC CCTGTTTTGT GCAACC;
  e) a nucleic acid, designated env5, having the following nucleotide sequence;
  GATGATTATC AGGAAATAAC TTTGAATGTA ACA-GAGGCTT TTGATGCATG GAATAAT;
  f) a nucleic acid, designated env6, having the following nucleotide sequence;
  GAGACATCAA TAAAACCATG TGTGAAACTA ACAC-CTTTAT GTGTAGCAAT GAAATGC;
  g) a nucleic acid, designated env7, having the following nucleotide sequence;
  AACCATTGCA ACACATCAGT CATCACAGAA TCAT-GTGACA AGCACTATTG GGAT;
  h) a nucleic acid, designated env8, having the following nucleotide sequence;
  GCTATAAGGT TTAGATACTG TGCACCACCG GGT-TATGCCC TATTAAGATG TAATGATACC;
  i) a nucleic acid, designated env9, having the following nucleotide sequence;
  AAAAGACCCA GACAAGCATG GTGCTGGTTC AAAGGCAAAT GGAAAGAC;
  j) a nucleic acid, designated env10, having the following nucleotide sequence;
  A A A G G C T C A G A C C C A G A A G T A G C A T A -C A T G T G G A C T A A C T G C A G A G -GAGAGTTTCTCTACTGCAACATGACTTG-GTTCCTCAAT; and
  k) a nucleic acid, designated env11, having the following nucleotide sequence;
  CGCAATTATG CACCGTGCCA TATAAAGCAA ATAAT-TAACA CATGGCATAA GGTAGGGAGA AATGTATAT.
3. An isolated or purified envelope protein of HIV-2 having the following amino acid sequence;

Met Met Asn Gln Leu Leu Ile Ala Ile Leu Leu Ala Ser Ala Cys

Leu Val Tyr Cys Thr Gln Tyr Val Thr Val Phe Tyr Gly Val Pro

Thr Trp Lys Asn Ala Thr Ile Pro Leu Phe Cys Ala Thr Arg Asn

Arg Asp Thr Trp Gly Thr Ile Gln Cys Leu Pro Asp Asn Asp Asp

Tyr Gln Glu Ile Thr Leu Asn Val Thr Glu Ala Phe Asp Ala Trp

Asn Asn Thr Val Thr Glu Gln Ala Ile Glu Asp Val Trp His Leu

Phe Glu Thr Ser Ile Lys Pro Cys Val Lys Leu Thr Pro Leu Cys

Val Ala Met Lys Cys Ser Ser Thr Glu Ser Ser Thr Gly Asn Asn

Thr Thr Ser Lys Ser Thr Ser Thr Thr Thr Thr Thr Pro Thr Asp

Gln Glu Gln Glu Ile Ser Glu Asp Thr Pro Cys Ala Arg Ala Asp

Asn Cys Ser Gly Leu Gly Glu Glu Glu Thr Ile Asn Cys Gln Phe

Asn Met Thr Gly Leu Glu Arg Asp Lys Lys Lys Gln Tyr Asn Glu

Thr Trp Tyr Ser Lys Asp Val Val Cys Glu Thr Asn Asn Ser Thr

Asn Gln Thr Gln Cys Tyr Met Asn His Cys Asn Thr Ser Val Ile

Thr Glu Ser Cys Asp Lys His Tyr Trp Asp Ala Ile Arg Phe Arg

Tyr Cys Ala Pro Pro Gly Tyr Ala Leu Leu Arg Cys Asn Asp Thr

Asn Tyr Ser Gly Phe Ala Pro Asn Cys Ser Lys Val Val Ala Ser

Thr Cys Thr Arg Met Met Glu Thr Gln Thr Ser Thr Trp Phe Gly

Phe Asn Gly Thr Arg Ala Glu Asn Arg Thr Tyr Ile Tyr Trp His

Gly Arg Asp Asn Arg Thr Ile Ile Ser Leu Asn Lys Tyr Tyr Asn

Leu Ser Leu His Cys Lys Arg Pro Gly Asn Lys Thr Val Lys Gln

Ile Met Leu Met Ser Gly His Val Phe His Ser His Tyr Gln Pro

Ile Asn Lys Arg Pro Arg Gln Ala Trp Cys Trp Phe Lys Gly Lys

Trp Lys Asp Ala Met Gln Glu Val Lys Thr Leu Ala Lys His Pro

Arg Tyr Arg Gly Thr Asn Asp Thr Arg Asn Ile Ser Phe Ala Ala

Pro Gly Lys Gly Ser Asp Pro Glu Val Ala Tyr Met Trp Thr Asn

Cys Arg Gly Glu Phe Leu Tyr Cys Asn Met Thr Trp Phe Leu Asn

Trp Ile Glu Asn Lys Thr His Arg Asn Tyr Ala Pro Cys His Ile

-continued

Lys Gln Ile Ile Asn Thr Trp His Lys Val Gly Arg Asn Val Tyr

Leu Pro Pro Arg Glu Gly Glu Leu Ser Cys Asn Ser Thr Val Thr

Ser Ile Ile Ala Asn Ile Asp Trp Gln Asn Asn Asn Gln Thr Asn

Ile Thr Phe Ser Ala Glu Val Ala Glu Leu Tyr Arg Leu Glu Leu

Gly Asp Tyr Lys Leu Val Glu Ile Thr Pro Ile Gly Phe Ala Pro

Thr Lys Glu Lys Arg Tyr Ser Ser Ala His Gly Arg His Thr Arg

Gly Val Phe Val Leu Gly Phe Leu Gly Phe Leu Ala Thr Ala Gly

Ser Ala Met Gly Ala Arg Ala Ser Leu Thr Val Ser Ala Gln Ser

Arg Thr Leu Leu Ala Gly Ile Val Gln Gln Gln Gln Gln Leu Leu

Asp Val Val Lys Arg Gln Gln Glu Leu Leu Arg Leu Thr Val Trp

Gly Thr Lys Asn Leu Gln Ala Arg Val Thr Ala Ile Glu Lys Tyr

Leu Gln Asp Gln Ala Arg Leu Asn Ser Trp Gly Cys Ala Phe Arg

Gln Val Cys His Thr Thr Val Pro Trp Val Asn Asp Ser Leu Ala

Pro Asp Trp Asp Asn Met Thr Trp Gln Glu Trp Glu Lys Gln Val

Arg Tyr Leu Glu Ala Asn Ile Ser Lys Ser Leu Glu Gln Ala Gln

Ile Gln Gln Glu Lys Asn Met Tyr Glu Leu Gln Lys Leu Asn Ser

Trp Asp Ile Phe Gly Asn Trp Phe Asp Leu Thr Ser Trp Val Lys

Tyr Ile Gln Tyr Gly Val Leu Ile Ile Val Ala Val Ile Ala Leu

Arg Ile Val Ile Tyr Val Val Gln Met Leu Ser Arg Leu Arg Lys

Gly Tyr Arg Pro Val Phe Ser Ser Pro Pro Gly Tyr Ile Gln ***

-continued

Ile His Ile His Lys Asp Arg Gly Gln Pro Ala Asn Glu Glu Thr

Glu Glu Asp Gly Gly Ser Asn Gly Gly Asp Arg Tyr Trp Pro Trp

Pro Ile Ala Tyr Ile His Phe Leu Ile Arg Gln Leu Ile Arg Leu

Leu Thr Arg Leu Tyr Ser Ile Cys Arg Asp Leu Leu Ser Arg Ser

Phe Leu Thr Leu Gln Leu Ile Tyr Gln Asn Leu Arg Asp Trp Leu

Arg Leu Arg Thr Ala Phe Leu Gln Tyr Gly Cys Glu Trp Ile Gln

Glu Ala Phe Gln Ala Ala Ala Arg Ala Thr Arg Glu Thr Leu Ala

Gly Ala Cys Arg Gly Leu Trp Arg Val Leu Glu Arg Ile Gly Arg

Gly Ile Leu Ala Val Pro Arg Arg Ile Arg Gln Gly Ala Glu Ile

Ala Leu Leu *** Gly Thr Ala Val Ser Ala Gly Arg Leu Tyr Glu

Tyr Ser Met Glu Gly Pro Ser Ser Arg Lys Gly Glu Lys Phe Val

Gln Ala Thr Lys Tyr Gly.

4. A method for producing a protein as claimed in claim 3, comprising providing a transformed host containing a DNA coding for the protein and expressing the protein.

5. An isolated or purified subgenomic HIV-2 nucleic acid, designated gag1, capable of encoding for a segment of the Gag protein, said nucleic acid having the following nucleotide sequence:

GACGTAAA TTAGTGCTAA AAGGACTAGG GATGAACCCT ACCTTAGAAG AGAATGCTGA CCGCC.

6. A method for producing a peptide comprising providing a transformed host containing a DNA coding for a subgenomic HIV-2 nucleic acid, as claimed in claim 2 or claim 5, and expressing the peptide.

* * * * *

UNITED STATES PATENT AND TRADEMARK OFFICE

CERTIFICATE OF CORRECTION

PATENT NO. : 5,770,703

DATED : June 23, 1998

INVENTOR(S) : Marc ALIZON et al.

It is certified that error appears in the above-identified patent and that said Letters Patent is hereby corrected as shown below:

Claim 1, col. 36, line 1, "GAAT" should be --CAAT--.

Signed and Sealed this

Thirteenth Day of October 1998

Attest:

Bruce Lehman

BRUCE LEHMAN

*Attesting Officer*

*Commissioner of Patents and Trademarks*